United States Patent [19]

Garvin et al.

[11] Patent Number: 5,200,327
[45] Date of Patent: Apr. 6, 1993

[54] EXPRESSION SYSTEM FOR THE SECRETION OF BIOACTIVE HUMAN GRANULOCYTE MACROPHAGE COLONY STIMULATING FACTOR (GM-CSF) AND OTHER HETEROLOGOUS PROTEINS FROM STREPTOMYCES

[75] Inventors: Robert T. Garvin, Toronto; Lawrence T. Malek, Brampton, both of Canada

[73] Assignee: Cangene Corporation, Mississauga, Canada

[21] Appl. No.: 224,568

[22] Filed: Jul. 26, 1988

Related U.S. Application Data

[63] Continuation-in-part of Ser. No. 795,331, Nov. 6, 1985, abandoned, and a continuation-in-part of Ser. No. 221,346, Jul. 18, 1988, abandoned.

[30] Foreign Application Priority Data

Jul. 25, 1988 [CA] Canada ................................. 572956

[51] Int. Cl.$^5$ ...................... C12P 21/02; C12N 15/76; C12N 15/00; C12N 1/21
[52] U.S. Cl. .................................. 435/69.5; 435/69.1; 435/172.3; 435/252.3; 435/320.1; 536/23.5; 935/48; 935/60; 530/399
[58] Field of Search .............. 536/27; 435/69.1, 172.3, 435/320.1, 69.5; 935/39, 40, 41, 48, 60, 252.3

[56] References Cited

U.S. PATENT DOCUMENTS

| | | | |
|---|---|---|---|
| 4,338,397 | 7/1982 | Gilbert et al. | 435/69.1 |
| 4,745,056 | 5/1988 | Guterman et al. | 435/69.1 |
| 4,783,415 | 11/1988 | Hoshiko et al. | 435/320.1 |

OTHER PUBLICATIONS

Henderson: "Characterization and Structure of Genes for Proteases A and B from *Streptomyces griseus*", *J. Bacteriology*, 169:3778–3784 (1987).

Bibb et al. "The Agarase Gene (dagA) of *Streptomyces coelicolor* A3(2): Affinity Purification . . . ", *J. Gen Microbiol.* 133: 2089–2096 (1987).

Jurasek et al. "Amino Acid Sequence of *Streptomyces griseus* Protease B, A Major Component of Pronase", *Biochem. and Biophysical Research Communications*, 61(4): 1095–1100 (1974).

Duez et al., "Primary Structure of the Streptomyces R61 Extracellular DD-Peptidase . . . ", *Eur. J. Biochem.*, 162: 509–518 (1987).

Burgess et al., "Purification and Properties of Bacterially Synthesized Human Granulocyte-Macrophage Colony Stimulating Factor", *Blood*, 58: 43–51.

Chang "Engineering for Protein Secretion in Gram-Positive Bacteria", *Methods in Enzymology*, 153: 507–517 (1987).

Ernst et al. "O-Glycosylation and Novel Processing Events During Secretion Of α-Factor/GM-CSF Fusions By *Saccharomyces cerevisiae*, Biotechnology", 5: 831–834 (1987).

Lee et al., "Isolation Of cDNA For A Human Granulocyte-Macrophage Colony-Stimulating Factor By Functional Expression in Mammalian Cells", *Proc. Natl. Acad. Sci. USA*, 82: 4360–4364 (1985).

Moonen et al., "Increased Biological Activity of De- (List continued on next page.)

Primary Examiner—Richard A. Schwartz
Assistant Examiner—S. L. Nolan
Attorney, Agent, or Firm—Foley & Lardner

[57] ABSTRACT

A gene expression system is used to produce heterologous biologically active proteins, in particular bioactive granulocyte macrophage colony stimulating factor ("GM-CSF"), secreted from a host selected from the Streptomyces genera. The gene expression system includes a regulatory nucleotide sequence linked to a second nucleotide sequence encoding the heterologous protein. The regulatory sequence, encodes a peptide which directs the secretion of the heterologous protein in bioactive form from a host selected from the Streptomyces genera. The regulatory sequence includes a signal sequence and a promoter sequence. The second nucleotide sequence, which encodes GM-CSF or a biologically active derivative of GM-CSF, may be either natural or synthetic. In particular, the invention relates to an expression system for secreting bioactive, non-glycosylated, oxidized, therapeutically useful GM-CSF from a host selected from the Streptomyces genera.

21 Claims, 22 Drawing Sheets

OTHER PUBLICATIONS glycosylated Recombinant Human Granulocyte/Macrophage Colony-Simulating...", *Proc. Natl. Acad. Sci. USA*, 84: 4428–4431 (1987).

Robbins et al., "Primary Structure of the Streptomyces Enzyme Endo-β-N-Acetylglucosaminidase H", *J. Biol. Chem.*, 259: 7577–7583 (1984).

Sjostrom et al. "Signal Peptide Amino Acid Sequences In *Escherichia coli* Contain Information Related to Final Protein Localization . . ." *EMBO J.*, 6(3): 823–831 (1987).

Wong et al., "Human GM-CSF: Molecular Cloning Of The Complementary DNA And Purification Of The Natural And Recombinant Proteins", *Science* 228: 810–814 (1985).

FIG. 1A

```
       Pst I                                              Bal I
       GCCCCCGCCCGGTCGCCC TCGCCGTCGACCCAGCCGTGGGAGCACGTCAACGCGAT
       ---:-.----+----:----.----+----:----.----+----:----.----+  60
       ACGTCGGGGGCGGGCCAGCGGGAGCAGCTGGGTCGGCCACCCTCGTGCAGTT GCGCTA

CCAGGAGGCCCCGCTCAACCTCTC GCGGGACACGGCCCGAGATGAACGAGAC
       ---:-.----+----:----.----+----:----.----+----:----.----+ 120
       GGTCCTCCGGGGCGGGACGAGTTGGAGAGCGCCCTGTGC CGGCGGGCTCTACT TGCTCTG

CGTGGAGGTGATCTCGGAG ATGTTCGACTTGCAGGAGCCCACGTGCCTCCAGACCCGCCT
       ---:-.----+----:----.----+----:----.----+----:----.----+ 180
       GCACCTCCACTAGAGCCTC TACAAGCTGAACGTCCTCGGGTGCACGGAGGTCTGGGCGGA

CGAGCTGTACAAGCAGGGGCTCCGGGCAGCCTCACCAAGCTCAAGGGCCGCTGACCAT
       ---:-.----+----:----.----+----:----.----+----:----.----+ 240
       GCTCGACATGTTC GTCCCCGAGGCCCCGTCGGAGTGGTTCGAGT TCCCGGACTGGTA
```

FIG. 1B

```
GATGGGCGTCCCACTACAAACAGCACTGCCCCCC ACGCCGGAGACGTCGTGCGCCACCCA
-----:----+----:----+----:----+----:----+----:----+----:----+  300
CTACCCGCAGGGGTGATGTT TGTCGTGACGGGGGG TGCGGCCTC TGCAGCACGCGGGTGGGT

GATCATCACGTTCGAGTCG TTCAAGGAGAACCTGAAGGACTTCCTCC TCGTGATCCCC CTT
-----:----+----:----+----:----+----:----+----:----+----:----+  360
CTAGTAGTGCAAGCTCAGCAAGTTCC TCTTGGACT TCCTGAAGGAGGAGCACTAGGGGAA

Hind III
CGACTGCTGGGAGCCGGTGTGCAGGAGTGA
-----:----+----:----+----:--  392
GCTGACGACCCTCGGGCACGTCCTCACT TCGA
```

FIG 3B(1)

```
BamHI
GATCCGGGCCGTT TCCCGCGCCGCCCGGCCCACG TGGCGGTGGGGATTCCGGCCGAA
----+----:----+----:----+----:----+----:----+----:----+  60
          GCCGGCAAAGGGCGGGCCCGGCCACCCC TAAGGCCGGCTT

CGGCCCGACGCCCATGTGACGCCTGCGTGC TGCGGCGCCCGCCGCGCAGGCTCGCCG
----+----:----+----:----+----:----+----:----+----:----+ 120
GCCGGGCTGCGGGTACACTGGGCACGACGCACGACGCGCGCGGCGTCCGAGCGGC

GGGCGGAGACCCGGACCCGCGAGGTCC TCGCCGCCGACCGGGAGGCGTGCGGCCTCG
----+----:----+----:----+----:----+----:----+----:----+ +180
CCCGCCCTGGGCCTGGCCCGGCGGGCT CCAGGAGCGGCCCC TCCGCACGCCGGAGC

CCGCGAGACCGCCGTCCTGCTGCCGC TCACGGAGGCGTACCTC TCGCCCTGCGCGGGC
----+----:----+----:----+----:----+----:----+----:----+ 240
GGCGCTCTGGCGGCAGGACGACGCCGAGTGCC TCCGCATGGAGAGCGGGACGCGCCCG

CCTCG ACCCCCGCCGGGACCTCCGGCACGCGGGCGCACCGGGTC
----+----:----+----:----+----:----+----:----+ +300
GGAGCT GGGGGCGGCCCTGGAGGCCGTGCGCCCGGCGCTGGCCCAG
```

FIG 3B(2)

```
                                                                              360
CGCGGGCGCCCCCACCCCGC ACAAGAATGTCCGAAACCCTACGGGCCCCGACGAAAGG
---:--:--:--:--:--:--+--:--:--:--:--:--:--+--:--:--:--:--:--:--+--:--:--:--:--:--:--+--:--:--:--:--:--:--+--:--:--:--:--:--:--+
GCGCCCGCGGGGGGTGGGGG TGTTCTTACAGGCTTTGGGATGCCCCGGGGCTGCTT TCC

420
CGCGGAACGGGCGTC TCCGCC TCTGCCATGATGCCGCCCATGAGGATCAAGCGCACCAGCA
---:--:--:--:--:--:--+--:--:--:--:--:--:--+--:--:--:--:--:--:--+--:--:--:--:--:--:--+--:--:--:--:--:--:--+--:--:--:--:--:--:--+
GCGCCCTTGCCCG CAGAGGCGGAGAACGGTACTACGGCGGTACTCCTAGTTCGCGTGGTCGT T

Mlu I                                                                480
ACCGCTCGAACGCGGCGAGACGCGTCCGCACCACCGCGTACTCGCGGGGCTCGCCGCCG
---:--:--:--:--:--:--+--:--:--:--:--:--:--+--:--:--:--:--:--:--+--:--:--:--:--:--:--+--:--:--:--:--:--:--+--:--:--:--:--:--:--+
TGGCGAGCTTGCGCCGT CTGCGCAGGCGTGGTGGCGCATGAGCGCCCCGAGCGGGGC

540
TCGCGGGCGCTGGCCGT TCCCACCGCCAATGCGAGCCCCGTCGCCC TCGCCGTCGA
---:--:--:--:--:--:--+--:--:--:--:--:--:--+--:--:--:--:--:--:--+--:--:--:--:--:--:--+--:--:--:--:--:--:--+--:--:--:--:--:--:--+
AGCGCCCGCGACCGGCAAGGGTGGCGGTTACGTCGGGGGCGGCCAGCGGGAGCGGCAGCT

600
CCCAGCCGTGGGAGCACGTCAACGCGGATCCAGGAGCGCCGCCTGCTCAACCTCTCGC
---:--:--:--:--:--:--+--:--:--:--:--:--:--+--:--:--:--:--:--:--+--:--:--:--:--:--:--+--:--:--:--:--:--:--+--:--:--:--:--:--:--+
GGGTCGGCACCCTCGTGCAGTT GCGCTAGGTCCTCCGGCGGCGGACGAGTTGGAGAGCG
```

FIG. 3B(3)

```
GGGACACGGCCGCCGAGATGAACGAGAGACCGTGGAGGTGATCTCGGAGATGT TCGACTTGC
----:----:----:----:----:----:----:----:----:----:----:----:+ 660
CCC TGTGCCGGCGGCTCTACT TGCTCTGGCACCTCCACTAGAGCCT CTACAAGCTGAACG

AGGAGCCCACGTGCCT CCAGACCCGCCTCGAGCTGTACAAGCAGGGGCTCCGGGGCAGCC
----:----:----:----:----:----:----:----:----:----:----:----:+ 720
TCC TCGGGTGCACGGAGGTCTGGGCGGAGCTCGACATGTTCGT CCCCGAGGCCCCGTCGG

TCACCAAGCTCAAGGGGCCGCTGACCATGATGGCGTCCCAC TACAAACAGCACT GCCCCC
----:----:----:----:----:----:----:----:----:----:----:----:+ 780
AGTGGTTCGAGTTC CCCGGCGACTGGTACTACCGCAGGGTGATG TTTGTCG TGACGGGGG

CCACGCCGGAGACGTC GTGCGCCACCCAGATCATCACGTT CGAGTCGTTCAAGGAGAACC
----:----:----:----:----:----:----:----:----:----:----:----:+ 840
GGTGCGGCCTCT GCAGCACGCGGTGGGTCT AGTAGTGCAAGCTCAGCAAGTTCCTCT TGG

HindIII
TGAAGGACTTC CTCC TCGTGATCCCCT TCGACTGCTGCTGGGAGCCGGTGCAGGAGTGA
----:----:----:----:----:----:----:----:----:----:----:----:+ 900
ACTTCCT GAAGGAGGAGCACTAGGGGAAGCTGACGACGACCCTCGGCCACGTCC TCACTTCGA
```

FIG 4B(1)

```
BamHI
GATCCGGGCCGTT TCCCGGCGCGT CCCGCCGCCACGTGGCGCCGGTGGGGATTCCGGCC GAA
     ----+----:----+----:----+----:----+----:----+----:----+     60
GCCGGCAAAGGGCGCGCTGCGGGCGGTGCACCGCGGCCACCCCTAAGGCCGGC TT

CGGCCGACGCGCCCATGTGACCGCCTGCGTGC TGCGGCGTGCCCGCGCAGGCTCGCCG
     ----+----:----+----:----+----:----+----:----+----:----+    120
GCCGGCTGCGCGGGTACACTGGCGGACGCACGACGCCGCACGGGCGCGTCCGAGCGGC

GGGCGGGACCCGGACCCGGCTGGCCCGAGGTCCTC GCCGCCGACCGGGAGGCGTGCGGCCTCG
     ----+----:----+----:----+----:----+----:----+----:----+    180
CCCGCCCT GGGCCTGGGCCGATGGGCTCCAGGAGCGGCTGGCCC TCCGCACGCCGGAGC

CCGCGAGACCGCCGTCCTGCTGCGGC TCACGGAGGCGTACCTC TCGCCCTGCCGCGGGGC
     ----+----:----+----:----+----:----+----:----+----:----+    240
GGCGCTCTGGCGGCAGGACGACGCCGAGTGCCTCC GCATGGAGAGCGGCGCGCCCG

CCTCGACCCCGCGGGACCTCCGGCACCGGGGCCGGGGGCGACGCGGCACCGGGTC
     ----+----:----+----:----+----:----+----:----+----:----+    300
GGAGCTGGGCCCTGGAGGCCGTGCGGCCCCGGGCCGCCCCGCTGGCCGTGGCCCAG
```

FIG 4B(2)

```
CGCCGGGGCGCCCCCACCCCGCACAAGAATGTCCGAAACCCTACGGGCCCCGACGAAAGG
----+----:----+----:----+----:----+----:----+----:----+  360
GCGGGCCCCGCGGGGGGTGGCGTGTTCTTACAGGCTTTGGGATGCCCGGGGCTGCTTTCC

CGGGAACGGGCGTCTCCGCCTCTGCCATGATGCCGCCCATGAGGATCAAGGCACCAGCA
----+----:----+----:----+----:----+----:----+----:----+  420
GCGCCTTGCCGCGAGAGGCGGAGACGCGTACTACGGGGTACTCCTAGTTCCGGTCGT

Mlu I
ACCGCTCGAACGCGGCGAGACGCGTCCGCACCGCGCCCTGGCCCTCTCCGCTGCCGCCG
----+----:----+----:----+----:----+----:----+----:----+  480
TGGCGAGCTTGCGCCGCTCTGCGCAGGCGTGGCGCGGGACCGGGAGAGGCGACGGCGGC

Pst I
CGCTCGTGTGGGGTCGACGGCGCCGCCTCCGGGGCGTCTGCAGCCCCGCGTCGCCCT
----+----:----+----:----+----:----+----:----+----:----+  540
GCGAGCACGACCCCAGCTGCCGCGGCGGAGGCCCCGCAGACGTCGGGGCGCCAGCGGGA

CGCCGTCGACCCAGCCGTGGGAGCACGTCAACGCGATCCAAGGAGGCCCGCCTGCTCA
----+----:----+----:----+----:----+----:----+----:----+  600
GCGGCAGCTGGGTCGGCACCCTCCGGTAGGTCCTAGGTCCTCCGGGGACGGGACGAGT
```

FIG. 4B(3)

```
ACCTCTCGCGGGACACGGCCGCCGCCGAGAT GAACGAGACCGTGGAGGTGATCTCGGAGATGT
....+....:....+....:....+....:....+....:....+....:....+....:  + 660
TGGAGAGCGCCCTGTGCCGGCGGCTC TACT TGCTC TGGCACCTCCACTAGAGCCTCTACA

TCGACTTGCAGGAGCCCACGTGCCTCC AGACCCGCCTCGAGCTG TACAAGCAGGGGCTCC
....+....:....+....:....+....:....+....:....+....:....+....:  + 720
AGCTGAACGTCCTCGGGTGCACGGAGGTC TGGGCGGAGCTCGACATGT TCGTCCCGAGG

GGGGCAGCCTCACCAAGCTCAAGGGGCCGCTGACCATGATGGCGTCCCACTACAAACAGC
....+....:....+....:....+....:....+....:....+....:....+....:  + 780
CCCCGTCGGAGTGGTTCGAGTTCCCCGGCGACTGGTACTACCGCAGGGTGATGTT TGTCG

ACTGCCCCCCC ACGCCGGAGAGACGTCGTGCGCCACCCAGATCATCACGTTCGAGTCG TTCA
....+....:....+....:....+....:....+....:....+....:....+....:  + 840
TGACGGGGGGGTGCGGCCTC TGCAGCACGCGGTGGGTCTAGTAGTGCAAGCTCAGCAAGT

HindIII
AGGAGAACCTGAAGGACTTCC TCCTCG TGATCCCC TTCGACTGCTGGGAGCCGGGTGCAGGAGTGA
....+....:....+....:....+....:....+....:....+....:....+....:  --- 909
TCC TCTTGGACTTCC TGAAGGAGGAGCACTAGGGGAAGCTGACGACCCTCGGCC ACGTCCTCACTTCGA
```

FIG 5B(1)

```
BamHI
GATCCGGCCGTT TCCCGCGCCACG TGGGCGGTGGG GATTCCGGCCGAA
- - -+- - - - +- - - - +- - - - +- - - - +- - - - +  60
GCCGGCAAAGGG CGCGGTGCACC CGCCACCCCTAAGGCCGGC TT

CGGCCGACGCC CCATGTGACCG CTGCGCGGTG CTGCGCGGCCCG GCGGCTCGCCG
- - -+- - - - +- - - - +- - - - +- - - - +- - - - +  120
GCCGGCTGCGG GGGTACACTGG CGACGCGCCAC GACGCGCCGGGC CGCGAGCGGC

GGGCGGGACCC GGACCCGGAC CCGCCGAGGT CCTC GCCGCGACCGGGAGGC GTGCGGCCTCG
- - -+- - - - +- - - - +- - - - +- - - - +- - - - +  +180
CCCGCCCTGGG CCTGGGCCTG GGCGGCTCCAGGAGCGGGCCCTC CGCACGCCGAGC

CCGCGAGACCGCCGTCCT GCTGCGGG CTCACGAGGGCGTACCTCTC GCCCTGCGCGGGC
- - -+- - - - +- - - - +- - - - +- - - - +- - - - +  +240
GGCGCTCTGGCGGCAGGA CGACGCCC GAGTGCTCCGCAT GGAGAGCGGCGCGCCCG

CCTCGACCCCCGCGGGACC TCCGCACCGGGACC GCCGGGCGCACCGGGTC
- - -+- - - - +- - - - +- - - - +- - - - +- - - - +  +300
GGAGCTGGGGGCGCCCTGAGGCCGTGGAGGCCGTGGAGC TGCGGCCCGCGTGGCCCAG
```

FIG. 5B(2)

```
CGCCGGCGCCCCCCACCCCGCAC AAGAATGTCCGAAACCCTACGGGCCCCGACGAAAGG
----:----:----:----:----:----:----:----:----:----:----:----:  + 360
GCGGCCGCGGGGGGTGGGGCGTGT TCTTACAGGCTT TGGGATGCCCGGGGCTGCTT TCC

CGCGGAACGGGCGTC TCCGCCT CTGCCATGATGCCGCCCATGAGGATCAAGCGCACCAGCA
----:----:----:----:----:----:----:----:----:----:----:----:  + 420
GCGCCT TGCCGCAGAGGCGGAGACGGTACTACGGGGTACTCCTAGTTCGCGTGGTCGT

Mlu I
ACCGCTCGAACGCGCCGAGACGCGTCCGCACCACCGCCGTACTCGC GGGGCTCGCGCCG
----:----:----:----:----:----:----:----:----:----:----:----:  + 480
TGGCGAGCTTGCGCGGCTC TGCGCAGGCGCATGAGCGCCCCGAGCGGGGGC

Nsi I            Xba I
TCGCGGGCTGGCCGT TCCCACCGGCCAATGCATTCC CGACCATCCCGCTGT
----:----:----:----:----:----:----:----:----.....   535
AGCGCCCGGACCGGCAAGGGTTACGTAAGGGCTGGTAGGGGCGACAGATC

Hind III
                                    CTAGCAAGCTTG
                                    --:----:----   547
                                    GTTCGAACGATC
```

FIG. 6B(1)

```
BamHI
GATCCGGCC GTTTCCCGGCGCCGCCC GCGCCCACGTGGGCGGTGGGGGATTCCGGGCCGAA
 ---:--:-+---:--:-+---:--:-+---:--:-+---:--:-+---:--:-+  60
GCCGGCAAAGGGCGCGGCGCGGGTGCACCGCGCCACCCCCTAAGGCCGGCTT

CGGCGCCGACGCCCCATGTGACCGCTGCGTG CTGCGGCGCCCGCGCAGGCTCGCCG
 ---:--:-+---:--:-+---:--:-+---:--:-+---:--:-+---:--:-+ +120
GCCGCGGCTGCGGGGTACACTGGCGACGCACGACGCGCCGGGCGCGTCCGAGCGGC

GGGCGGGACCCGGACCGGCCCGCCGAGGTCCTC GCCGCCGGGACCGGAGGCGTGCGGGCCTCG
 ---:--:-+---:--:-+---:--:-+---:--:-+---:--:-+---:--:-+ +180
CCCGCCCTGGG CCTGGGCCGGCTCCAGGAGCGGCGGCTCCAGG CACGCCGGAGC

CCGGAGAGACCGCCGTCCTGCTGCGGC TCACGGAGGCGTACCTC TCGCCCTGCGCGGGC
 ---:--:-+---:--:-+---:--:-+---:--:-+---:--:-+---:--:-+ +240
GGCGCTCTGGCGGCAGGACGACGCCGAGTGCC TCCGCATGGAGAGAGACGGCCCCG

CCTCGACCCCGCGGACCTCCCGGACCCGGGCGACGCCCGGGCGCACCGGGTC
 ---:--:-+---:--:-+---:--:-+---:--:-+---:--:-+---:--:-+ +300
GGAGCTGGGGCGGCCCTGGAGGCCGTGGGGCGCCCCGGCTGCCCGGCCCAG
```

FIG. 6B(2)

```
                                                                              360
CGCGGGGCGCCCCCACCCCGC ACAAGAATGTCCGAAACCCTACGGGCCCCGACGAAAGG
----+---------+---------+---------+---------+---------+
GCGCCCCGCGGGGGTGGGGCG TGTTCTTACAGGCT TTGGGATGCCCGGGGCTGCTT TCC

420
CGCGGAACGGCGTCTC CGCCTC TGCCATGATGCCGCCCATGAGGATCAAGCGCACCAGCA
----+---------+---------+---------+---------+---------+
GCGCCT TGCCGCAGAGGCGGAGAACGGTACTACGGCGGGTACTCCTAGTTCG CGTGGTCGT

Mlu I
ACCGCTCGAAACGGCGTCCGCACCGCGGCCCTGGCCC TCTCCGCT GCCGCCG          +480
----+---------+---------+---------+---------+---------+
TGGCGAGCTTGCGCCGCT CTGCGCAGGGCGTGGCCGCCGGGAGAGGCGACGGCGGGC

Pst I
CGCTCG TGCTGGGGTCGACGGCCGCCTCCGGGGCGTCTGCAGAGATCACTAGAATCCCAT    540
----+---------+---------+---------+---------+---------+
GCGAGCACGACCCCAGCTGCCGGCGGAGGCCCCGCAGACGTCTCTAGTGATCTTAGGGTA

600
TGT ACAAGGGGTAAGTCTT TGAGAAAGGCCTTGAAAG GAACACGGTTT GTTGGAAGACTTCT T
----+---------+---------+---------+---------+---------+
ACATGT TCCCAT TCAGAAACTCT TTCCGGAACT TCTT TGTGCCAAACAACCT TCTGAAGA
```

FIG. 6B(3)

```
TGCAAAAGCAACAATACGGTATCTCC TCCAAGTACTCTGGTT TCGGTGAAGTCGCTTCCG
- - - : - - - : - - - + - - - : - - - : - - - + - - - : - - - : - - - + - - - : - - - : - - - + - - - : - - - : - - - + - - - : - - - : - - - +  660
ACGTTT TCGTTGT TATGCCATAGAGGAGGTTCATGAGACCAAAGCCACTTCAGCGAAGGC

TTCCAT TGACCAACTACTTGGACTCCCAATACTTCGGTAAGATCTACTTAGGTACCCCAC
- - - : - - - : - - - + - - - : - - - : - - - + - - - : - - - : - - - + - - - : - - - : - - - + - - - : - - - : - - - + - - - : - - - : - - - +  720
AAGGTAACTGGTTGTGATGAACCTGAGGGGTTATGAAGCCATTCTAGATGAATCCATGGGGTG

CACAAGAATTCACTG TCTTGT TCGACACCGGTTCTTCTGACT TC TGGGTCCCATCGATT T
- - - : - - - : - - - + - - - : - - - : - - - + - - - : - - - : - - - + - - - : - - - : - - - + - - - : - - - : - - - + - - - : - - - : - - - +  780
GTGT TCTTAAGTGACAGAACAAGCTGTGGCCAAGAAGACTGAAGACCCAGGGTAGCTAAA
                                                        Sac I  Xba I

ACTGTAAGTCCAACGCTTGTAAGAACCACCAAAGATTCGACCCAAGAAAGAGCT
- - - : - - - : - - - + - - - : - - - : - - - + - - - : - - - : - - - + - - - : - - - : - - - + - - - : - - -  838
TGACATTCAGGTTGCGAACATTCT TGGTGGTT TCTAAGCTGGGTTCTT TCTCGAGATC

Hind III
                                              CTAGCAAGCTTG
                                              - - - + - - - : - - - +850
                                              GTTCGAACGATC
```

FIG. 7B(1)

```
BamHI
GA TCCGGCCGT TCCCGGCCGCCCGCCCCACGTGGGCGCCGGTGGGGGATTCCGGCCGAA
   - - -+- - - . . - - -+ - - - . - - - + - - - . - - - + - - - . - - - + - - - . - - - + 60
   GCCGGCAAAGGGCGCGGCTGGGCGGCACCGCCACCCCCTAAGGCCGGCTT

CGCGCCGACGCCCATGTGACCGCCTGCGT GCTGCGCGCCCGGCGCCGCAGGCTCGCCG
- - - + - - - . - - - + - - - . - - - + - - - . - - - + - - - . - - - + - - - . - - - +120
GCGCGGCTGCGGGTACACTGGCGGACGCACGACGCGCCGGGCGCGTCCGAGCGGC

GGGCGGACCCGGACCCCGGACGGTCCTCGCC GCCGACCGGAGGCGTGCGGCCTCG
- - - + - - - . - - - + - - - . - - - + - - - . - - - + - - - . - - - + - - - . - - - +180
CCCGCCCTGGGC CTGGGCCGGCTCCAGGAGCGGCTGGCCCTCCGCACGCC GGAGC

CCGCGAGACCGCCGTCCTGCTGCGGCTCACGGAGGCGTACCTCTC GCCCTGCGCGGGC
- - - + - - - . - - - + - - - . - - - + - - - . - - - + - - - . - - - + - - - . - - - +240
GGCGCTCTGGCCGGCAGGACGACGCCGAGTGCCTCCGCATGGAGAGCGCGCCCG

CCTCGACCCCGCCCGGGACCTCCGGCACCCCGGCGACCGGCACCGGGTC
- - - + - - - . - - - + - - - . - - - + - - - . - - - + - - - . - - - + - - - . - - - +300
GGAGCTGGGGCGGGCCCTGGAGGCGCACCCGCCCGCTGCCCGTGGCCCAG
```

FIG 7B(2)

```
CGCCGGCGCCCCCACCCCGCACAAGAATGTCCGAAACCCTACGGGCCCCGACGAAAGG
----+----:----+----:----+----:----+----:----+----:----+----  360
GCGGCCGCGGGGGTGGGGCGTGTTCTTACAGGCTTTGGGATGCCCGGGGCTGCTTT CC

CGCGGAACGGGCGTCTCCGCCTCTGCCATGATGCGCCCATGAGGATCAAGGCGCACCAGCA
----+----:----+----:----+----:----+----:----+----:----+----  420
GCGCCTTGCCCGCAGAGGCGGAGACGGGTACTACGGGTACTCCTAGTTCGCGTGGTCGT

Mlu I
ACCGCTCGAACGCGGCGAGACGCGTCCGCACCACCGCTACTCGCGGGCTCGCCGCCG
----+----:----+----:----+----:----+----:----+----:----+----  480
TGGCGAGCTTGCGCCGCTCTGCGCAGGCGTGGTGGCGGCATGAGCCCCGAGCGGGCGGC

Pst I
TCGCGGGCGGCTGGCCGTTCCCACCGCGAACGCTGCAGAGATCACTAGAATCCCATTGTACA
----+----:----+----:----+----:----+----:----+----:----+----  540
AGCGCCCGGCGACCGGCAAGGGTGGCGCTTGCGACGTCTCTAGTGATCTTAGGGTAACATGT

AGGGTAAGTCTTTGAGAAAGGCCTTGAAGGAACACGGTTTGTTGGAAGACTTCTTGCAAA
----+----:----+----:----+----:----+----:----+----:----+----  600
TCCCATTCAGAAACTCTTTCCGGAACTTCCTTGTGCCAAACAACCTTCTGAAGAACGTTT
```

FIG 7B(3)

```
AGCAACAATACGGTATCTCCTCC AAGTACTC TGGTT TCGGTGAAGTCGCT TCCGT TCCAT
 ---:---:---:---:---:---+---:---:---:---:---:---+---:---:---:---:---:---+   660
TCGTT GTTATGCCATAGAGGAGGTTC ATGAGACCAAAGCCACT TCAGCGAAGGCAAGGTA

TGACCAACTACTTGGACTCCCC AATACTTCG GTAAGATCTACTTAGG TACCCCACCACAAG
 ---:---:---:---:---:---+---:---:---:---:---:---+---:---:---:---:---:---+   720
ACTGGTTGATGAACCTGAGGGT TATGAAGCC ATTC TAGATGAATCCATGGGGTGGTGT TC

AATTCACTGTCT TGTTCGACACCGG TTCTTCTGAC TTCTGGGTCCC ATCGATT TACTGTA
 ---:---:---:---:---:---+---:---:---:---:---:---+---:---:---:---:---:---+   780
TTAAGTGACAGAACAAGCTGTGGCCAAGAAGACTGAAGACCCAGGGTAGCTAAATGACAT

Sac I  Xba I
AGTCCAACGCTTGTAAGAACCACCAAAGATTCGACCCAAGAAAGAGCT
 ---:---:---:---:---:---+---:---:---:---:---:---+---  832
TCAGGTTGCGAACATTCTTGG TGGTT TCTAAGCTGGGTTCTT TCTCGAGATC
```

FIG. 8A

```
BamHI
GATCCGGCCGTT TCCCGCGCCGGCCGCC CACGTGGCGGTGGGGGATTCCGGCCGAA
........+.........+.........+.........+.........+.........+  60
         GCCGGCAAAGGGCGCGGCCGCCACCCCCTAAGGCCGGCTT
         GCGGGCAAAGGGCGCGGCCGCCACCCCCTAAGGCCGGCTT

CGGCGCCGACGCCCATGTGACCGCCTGCG TGCTGCGGCCCGCGCCGCAGGCTCGCCG
........+.........+.........+.........+.........+.........+  120
GCCGGGCTGTGGGTACACTGGCGGACGCGACGACGACGCGCGGCGTCCGAGCGGGC

GGGCGGACCCGGACCCGCCGAGGTCCTC GCCGCCGACCGGGAGGCGTGCGGCCTCG
........+.........+.........+.........+.........+.........+  180
CCCGCC TGGGCCTGGGCGGCTCCAGGAGCGGCCC TCCGCACGCCGGAGC

CCGCGAGACCGCCG TCCTGCT GCGGCTCACGGAGGCGTACC TCTCGCCCTGCGGGGC
........+.........+.........+.........+.........+.........+  240
GGCGCTCTG GCGGGCAGGACGACCGAGTGCCTC CGCATGGAGAGCGGGACGCGGCCCG
```

FIG. 8B

```
                                                    HaeII
CCTCGACCCCCGCC GGGACCCTCC GGCACCGGGCCCGGGGCGACGCCGGGGCGCACCGGGGTC
:::::::::::::+:::::::::::+:::::::::::+:::::::::::+:::::::::::+:::::::::::+ +300
GGAGCTGGGGCGG CCCTGGAGGCC CGTGGCCCGGGCCCGC TGCGGCCCGCGTGGCCCAG

CGCCGGCGCGCCC ACCCCGCACAAGAATGTCCGAAACCCTACGGCCCCGACGAAAGG
:::::::::::::+:::::::::::+:::::::::::+:::::::::::+:::::::::::+:::::::::::+ +360
GCGGCCGCGCGGG TGGGGCGTG TTCTTACAGGCTT TGGGATGCCCGGGGCTGCTTTCC

NcoI
CGCGGAACGGGCGTCTCCGC CTC TGCCATGATGCCGCC
:::::::::::::+:::::::::::+:::::::::::+:::::::::::+ +401
GCGCCT TGCCGCAGAGAGGCGGAGACGGTACTACGGGCGGGGTAC
```

FIG. 9A

```
BamHI
GATCCACGCGCTGTGCCCGC CGTGCGCCT TGCGCCGATCACTTCATC TGCCCGTTCCCGC C
- - - - - - - - - + - - - - - - - - - + - - - - - - - - - + - - - - - - - - - + - - - - - - - - - + - - - - - - - - - + 60
         GTGCGCGACACGGG CGGAAGCGGGAAGCGGGACTAGTGAAGTAGAGGGCAAGGGCGG

CCCGGGCAACACGCTCGCCG CGGCCGGGTTTTGGCGGGGAGCGGAACCGGATCGACGCCTG
- - - - - - - - - + - - - - - - - - - + - - - - - - - - - + - - - - - - - - - + - - - - - - - - - + - - - - - - - - - + 120
GGGCCCGTTGTGC GAGCGGCCGGCCCGCCAAAACCGCCCCCCTCGCCT TGGCCTAGCTGCGGAC

ACCCGGCGGAGGCCCCACCGG CCCCGGCAGCCGCACGGCT CCCGGGGCCGGTGACGGATG
- - - - - - - - - + - - - - - - - - - + - - - - - - - - - + - - - - - - - - - + - - - - - - - - - + - - - - - - - - - + 180
TGGGGCCGCTCCGGGGTGGCCCGGAGCGCCGTCG GCGTGCCGGAGGGCCCGGGCC ACTGCCCTAC

TGACCCGCGTGGCCGAAAGGCATTC TTGCGCGTC CCCCGTCC CCCGGCCCCC TCGATACTCCGGT
- - - - - - - - - + - - - - - - - - - + - - - - - - - - - + - - - - - - - - - + - - - - - - - - - + - - - - - - - - - + 240
ACTGGGCGCACCGGCTTT CCGTAAGAACGCAGGGCCAGGGCCAGGCCAGGGAGCTATGAGGCCA

CAGGCGATTGTCAGGGGCACGGGCGAATTCGAAAA TCCGGACACAGGCCCCGACTGCGC CTCAC
- - - - - - - - - + - - - - - - - - - + - - - - - - - - - + - - - - - - - - - + - - - - - - - - - + - - - - - - - - - + 300
GTCGCTAACAGTCCCCG TGCCGCTTAAGCTT TAGGCCT GTCCGGGGGCTGACGCGGAGTG
```

FIG. 9B

```
GGGCCCCGCCACCCCACAGGAGGCCCCGATT CCCCTCGGAGGAACCCGAAGTGAGGATC
---:--:---:---+---:---:---:---+---:---:---:---+---:---:---:---+---:---:---:---+---:---:---:---+ 360
CCCGGGGCGGTGGGGTGTCCT CCCGGGGCTAAGGGGAGCCTCCT TGGGCTTCACTCCTAG

Mlu I

AAGCGCACCAGCAACACCGCTCGAACGCGGCGAGACGCGTCCGCACCACCGCCGTACTCGCG
---:--:---:---+---:---:---:---+---:---:---:---+---:---:---:---+---:---:---:---+---:---:---:---+ 420
TTCG CGTGGTCGTTGGGCGAGCTTGC GCCGCTCTGCGCAGGCGTGGTGGGCATGAGCGC

Hae II

GGGCTCGCGCCCGTC GCGCGTCTGGCCGTTCCC ACCGCGAAACGCCGAAACCCCCGGACG
---:--:---:---+---:---:---:---+---:---:---:---+---:---:---:---+---:---:---:---+---:---:---:---+ +480
CCCGAGCGCGGCAGCGCGCCGGCAAGGGTGGGCGC TTGCGGCTTTGGGGGGCCT GC

Pst I

TTCAGTGCC AACCAGGCTGCA
---:--:---:---+-- 501
AAGTCACGGT TGGTCCG
```

FIG. 10

```
      Hae II                    Nsl I                    Xba I
      TGGCCGTT CCCACCGCCAATGCAT TCCCGACCATCCCGCTGT
      ----:----+----:----+----:----+----:----+----:----+  50
      CGCGACCGGCAAGGGTGGCGGT TACGTAAGGGCTGGTAGGGCGACAGATC
```

FIG. 11

```
                                                 Mlu I
      CATGAGGATCAAGGCGCACCAGCAACCGCTCGAACGGCGGCGAGA
      ----:----+----:----+----:----+----:----+----:--  47
      TCCTAGT TCCGTGGT CGTTGGGCGAGCTTGCCGCCGC TCTGCGC
```

FIG. 12

```
      Hae II                                    Pst I
      TGGCCGTTCCCC ACCGGCGAACGCTGCA
      ----:----+----:----+----:----+  30
      CGCGACCGGCAAGGGTGGCGCT TGCG
```

FIG. 13

Mlu I
```
CGCGTCCGCACCGGCGGCCC TGGCCCTCTCCGC TGCCGCCG         40
....:....+....:....+....:....+....:....+
AGGCGTGGCCGCGGGGACCGGGAGAGGCGACGGGGGC
                                           Pst I
CGCTCG TGCTGGGGTCGACGGGCCTCCGGGGGTCTGCA             81
....:....+....:....+....:....+....:....+-
GCGAGCACGACCCCAGCTGCCGGAGGCCCCGCAG
```

FIG. 14

Mlu I
```
CGCGTGTGGAT CTCCCTCC TGTTCGCGC TCGCCCT GATC T       40
....:....+....:....+....:....+....:....+
ACACCTAGAGGAGGACAAGCGCGAGCGGGAC TAGA
                                           Pst I
TCACCATGGCCT TCGGGTCGACGTCCTCCGCCCAGGCTGCA          81
....:....+....:....+....:....+....:....+-
AGTGGTACCGGAAGCCCAGCTGCAGGAGGCGGGTCCG
```

EXPRESSION SYSTEM FOR THE SECRETION OF BIOACTIVE HUMAN GRANULOCYTE MACROPHAGE COLONY STIMULATING FACTOR (GM-CSF) AND OTHER HETEROLOGOUS PROTEINS FROM STREPTOMYCES

The present application is a continuation-in-part of application Ser. No. 06/795,331, filed Nov. 6, 1985, now abandoned. The present application is also a continuation-in-part of copending application Ser. No. 07/221,346, filed Jul. 18, 1988 now abandoned.

FIELD OF THE INVENTION

This invention relates to secretion of heterologous bioactive proteins, in particular, granulocyte macrophage colony stimulating factor ("GM-CSF") by an expression system inserted into a host selected from the Streptomyces genera.

BACKGROUND OF THE INVENTION

In producing commercially viable proteins, the ability of the microorganism to secrete the protein into the broth in bioactive form is important. However, there are many proteins encoded by genetically engineered DNA constructs which may not be secreted by the cells in which the DNA is expressed or which may not secrete the protein in bioactive form. If the protein is not secreted into the broth, downstream processing is necessary. This means that the cells must be harvested, the cell walls must be broken open, the desired proteins must be recovered in pure form and then such proteins must be chemically re-natured to restore their bioactivity. If the protein is secreted into the broth, but not in its bioactive form, the protein must be treated after secretion to restore its bioactivity.

Some cells and microorganisms carry out the biological equivalent of downstream processing by secreting proteins in bioactive form. The mechanism which directs the secretion of some proteins through the cellular exterior into the outside environment of the cell is not yet fully understood. For example, the species *Streptomyces griseus* secretes many extracellular proteins in bioactive form. It would be expedient if heterologous proteins of commercial value, whose bioactivity is a function of their particular three dimensional molecular structure, could be secreted from Streptomyces at the levels observed for natural extracellular proteins.

Some of the literature relating to genetically engineered DNA constructs has assumed that the production of a functional protein using the information contained in DNA was solved by decoding the DNA. This assumption was based on the principle that the information needed to specify the complex -three-dimensional structure of a protein molecule is contained in the primary amino acid sequence of the protein. However, Canadian Application No. 449,456 entitled *Production of Active Proteins Containing Cystine Residues* filed by Cangene Corporation on Nov. 1, 1985 illustrates that the bioactivity of certain proteins derived from genetically engineered DNA constructs is dependent upon the formation of correctly positioned disulphide bonds. A more effective means was sought than conventional methods for the expression of heterologous genes in a host cell or microorganism. Thus, that invention identified that heterologous proteins could be secreted from a host microorganism in bioactive form without resorting to downstream processing. The use of certain microorganisms in conjunction with an expression system facilitates the formation of disulphide bonds upon expression of the genetically engineered DNA construct. Bioactivity of engineered proteins having cystine residues as an integral and necessary portion of their active structure was achieved by using a regulatory nucleotide sequence selected from a cell or microorganism capable of expressing and excreting homologous disulphide-bonded proteins, the nucleotide sequence being operably linked to a second nucleotide sequence encoding a disulphide bond-containing heterologous protein. The regulatory nucleotide sequence encoded a protein which resulted in heterologous protein secretion from the cell or microorganism. The heterologous protein could be natural or designed.

In Canadian Patent Application no. 542,628 entitled *Characterization and Structure of Genes for Protease A and Protease B from Streptomyces Griseus* filed on Jul. 21, 1987 by Cangene Corporation, a homologous gene expression system was disclosed. That invention related to a regulatory nucleotide sequence which directed the secretion of Protease A and Protease B from *Streptomyces griseus*. Protease A and Protease B are naturally-occurring proteins in *Streptomyces griseus*, thus the terminology "homologous". That application disclosed the regulatory nucleotide sequence which was responsible for one type of homologous secretion in Streptomyces. A gene expression system responsible for homologous expression was useful in constructing various other expression systems for heterologous expression.

Granulocyte macrophage colony stimulating factor ("GM-CSF") is a protein which stimulates the production of white blood cells. GM-CSF holds great promise as a biopharmaceutical for use in association with cancer treatment to aid in the restoration of white blood cells. Naturally occurring GM-CSF is a glycoprotein containing 127 amino acids and two disulphide bonds. GM-CSF is present in only trace quantities in the natural human source, which has prevented detailed structural analysis of the naturally isolated protein. Thus, most of the structural data for the natural GM-CSF is obtained from analysis of the complementary DNA sequence and the expression of a complementary DNA clone in mammalian cells. The GM-CSF which is expressed in mammalian cells contains 127 amino acids and two disulphide bonds, and is present in different glycosylated forms ranging in size from 14 to 35 kilodaltons. Some forms of GM-CSF may contain two N-linked carbohydrate groups and/or three O-linked carbohydrate groups, which accounts for the apparent size heterogeneity.

In Moonen et al (1987) a process is described for the production of GM-CSF by secretion from chinese hamster ovary cells. The GM-CSF is secreted as a 26-kilodalton glycoprotein which is biologically active. However, the biological activity is increased 20-fold by enzymatically removing the carbohydrate groups, indicating that an unglycosylated form of GM-CSF should be superior for clinical use.

In Ernst et al (1987) a process is described for the production of GM-CSF by secretion from the yeast *Saccharomyces cerevisiae* by using the alpha mating factor precursor. The GM-CSF is secreted as a heterogeneous mixture of glycoproteins ranging in size from 35 to 100 kilodaltons. Only a fraction of the secreted GM-CSF had been correctly processed from the alpha mating factor precursor. The specific biological activity of the glycosylated GM-CSF made in yeast and in mammalian cells was approximately the same. However, the structure of the attached carbohydrate groups of the GM-CSF produced in yeast were different from the natural carbohydrate groups of the GM-CSF produced in mammalian cells.

In Burgess et al (1987) a process is described for the production of an unglycosylated GM-CSF-like polypeptide from the cytoplasm of *E. coli*. The GM-CSF-like polypeptide as isolated from the *E. coli* cells, had an amino terminal methionine, and was reduced, denatured, and biologically inactive. The conversion of the biologically inactive GM-CSF-like polypeptide isolated from *E. coli* to a bioactive form required oxidative renaturation in vitro. The renatured GM-CSF-like polypeptide was still not equivalent to an unglycosylated form of GM-CSF due to the presence of an amino-terminal methionine in the *E. coli* produced protein.

The GM-CSF which is secreted by mammalian cells or yeast is bioactive, but glycosylated. The GM-CSF which is isolated from *E. coli* is unglycosylated, but not bioactive. Thus, the conventional processes for producing GM-CSF require expensive, time consuming, or inefficient downstream processing to convert the form of GM-CSF from the culture to the bioactive, unglycosylated GM-CSF which is preferred for clinical use.

Consequently, a need exists for an expression system which will provide bioactive protein, in particular bioactive GM-CSF, upon secretion. Such a protein product would be different as a structure of matter than conventional protein products since structure determines bioactivity.

SUMMARY OF THE INVENTION

This invention relates to a number of expression systems directing the secretion of heterologous proteins, in particular, granulocyte macrophage colony stimulating factor ("GM-CSF") in bioactive form from a host selected from the Streptomyces genera. In this document, unless the context otherwise requires, "GM-CSF" means substantially pure, non-glycosylated, oxidized GM-CSF protein. The bioactive GM-CSF produced in accordance with this invention is not glycosylated, however, in other respects it mimics its natural counterpart. The GM-CSF of this invention, like its natural counterpart, has correctly positioned intramolecular disulphide bonds. The new product produced in accordance with this invention is termed GM-CSF noglytein. GM-CSF noglytein has full bioactivity upon secretion from the host organism, namely, a host selected from the Streptomyces genera and exhibits all of the structural features of the natural GM-CSF glycoprotein.

In accordance with this invention, a gene expression system is used having a regulatory nucleotide sequence linked to a second nucleotide sequence encoding a heterologous protein. The regulatory sequence includes a signal sequence and a promoter sequence. The signal sequence encodes a peptide which directs the secretion of the heterologous protein in bioactive form from a host selected from the Streptomyces genera. The second nucleotide sequence, which may be natural or synthetic or a combination of natural and synthetic sequences, encodes a heterologous protein.

The expression systems described direct the secretion from Streptomyces hosts of encoded protein in bioactive form. It is contemplated that the expression systems of this invention could be used in other hosts. In addition, these expression systems may be used to direct the secretion of heterologous proteins other than GM-CSF, in accordance with the teaching of this invention.

In particular, this invention relates to a gene expression system for the secretion of granulocyte macrophage colony stimulating factor ("GM-CSF") in bioactive form from a host selected from the Streptomyces genera. The gene expression system includes a regulatory nucleotide sequence linked to a second nucleotide sequence encoding GM-CSF. The regulatory sequence includes a signal sequence and a promoter sequence. The signal sequence encodes a peptide which directs the secretion of GM-CSF in bioactive form from a host selected from the Streptomyces genera. The second nucleotide sequence, which may be natural or synthetic or a combination of natural and synthetic sequences, may encode GM-CSF.

The signal sequence encodes a signal peptide which directs secretion of the heterologous protein from a host selected from the Streptomyces genera. The signal sequence may encode the signal peptide of *Streptomyces griseus* protease B, *Streptomyces plicatus* endo-B-N-acetylglucosaminidase H, a hybrid of any of these peptides, or any other signal peptide which directs secretion of the heterologous protein, in particular GM-CSF, from a host selected from the Streptomyces genera. The signal sequence may encode the signal peptides of gram positive bacteria, gram negative bacteria, or a hybrid of these peptides. Furthermore, the signal sequence may encode a hybrid of signal peptides of Streptomyces and other bacteria.

The promoter sequence, which directs the synthesis of an RNA encoding a fusion protein composed of the signal peptide joined to the amino terminus of the heterologous protein permits the specific binding of and transcription by at least one type of Streptomyces RNA polymerase holoenzyme. The promoter sequence may include a sequence from the aminoglycoside phosphotransferase gene ("aph") of *Streptomyces fradiae* which permits the specific binding of and transcription by at least one type of Streptomyces RNA polymerase holoenzyme.

The expression system is inserted into a vector capable of transformation and replication in Streptomyces, and the vector is inserted into a host selected from the Streptomyces genera.

According to another aspect of the invention, a process of producing granulocyte macrophage colony stimulating factor in bioactive form secreted from a host selected from the Streptomyces genera is used. The process includes linking a sequence encoding a peptide which directs secretion of GM-CSF in bioactive form and a sequence encoding GM-CSF, inserting the sequences into a vector capable of transformation and replication in Streptomyces, inserting the vector into a host selected from the Streptomyces genera, growing the transformed host, and recovering bioactive GM-CSF.

In accordance with the invention, a signal peptide fused to a heterologous protein is produced by heterologous expression in a host selected from the Streptomyces genera.

In accordance with the invention, a signal peptide fused to GM-CSF is produced by heterologous expression in a host selected from the Streptomyces genera.

In accordance with the invention, bioactive protein is produced by heterologous expression in a host selected from the Streptomyces genera.

In accordance with the invention, bioactive GM-CSF is produced by heterologous expression in a host selected from the Streptomyces genera.

Recombinant DNA derived GM-CSF is secreted in bioactive form from a suitable host, in particular, a host selected from the Streptomyces genera. The GM-CSF is unglycosylated and has intramolecular disulphide bonds upon secretion.

BRIEF DESCRIPTION OF THE DRAWINGS

With reference to the Figures, a variety of short forms have been used to identify restriction sites, deoxyribonucleic acids, vectors and related information. Standard nomenclature has been used in identifying all of these components as is readily appreciated by those skilled in the art.

Preferred embodiments of the invention are described with respect to the drawings, wherein:

FIG. 1. is the DNA sequence of the PstI-Hind III fragment encoding GM-CSF;

FIG. 2. illustrates the specific alterations of the vector pIJ680;

FIG. 3. is
(a) a restriction map of the expression vector pAPO.GMCSF; and
(b) the sequence of the inserted BamHI-HindIII DNA fragment;

FIG. 4. is
(a) a restriction map of the expression vector pAEO.GMCSF; and
(b) the sequence of the inserted BamHI-HindIII DNA fragment;

FIG. 5. is
(a) a restriction map of the expression vector pAPO.G (or pAPO.H); and
(b) the sequence of the inserted BamHI-XbaI (or BamHI-HindIII) DNA fragment;

FIG. 6. is
(a) a restriction map of the expression vector pAEO.SX (or pAEO.SH); and
(b) the sequence of the inserted BamHI-XbaI (or BamHI-Hind III) DNA fragment;

FIG. 7. is
(a) a restriction map of the expression vector pAPO.SX; and
(b) the sequence of the inserted BamHI-XbaI DNA fragment;

FIG. 8. is the sequence of the BamHI-NcoI DNA fragment containing the aph promoter;

FIG. 9. is the sequence of the BamHI-Pst DNA fragment of pPP1 containing the protease B promoter and encoding the protease B signal peptide and the amino-terminal 10 amino acids of the protease B pro-peptide;

FIG. 10. is the sequence of the HaeII-XbaI DNA fragment encoding the carboxy terminus of the protease B signal peptide and the amino terminus of human growth hormone;

FIG. 11. is the sequence of the DNA fragment encoding the amino terminus of the protease B signal peptide;

FIG. 12. is the sequence of the HaeII-PstI DNA fragment encoding the carboxy terminus of the protease B signal peptide;

FIG. 13. is the sequence of the MluI-PstI DNA fragment encoding the carboxy terminal 27 amino acids of the endo H signal peptide;

FIG. 14. is the sequence of the MluI-PstI DNA fragment encoding the carboxy terminal 25 amino acids of the apr signal peptide;

FIG. 15. is an analysis of the secretion of GM-CSF by
(a) polyacrylamide gel electrophoresis; and
(b) Western blotting.

DETAILED DESCRIPTION OF THE PREFERRED EMBODIMENTS

The present invention describes a process for the production of a biologically active form of human GM-CSF by direct secretion from Streptomyces by using an expression system. It also describes expression vectors which could be used for the production of other heterologous proteins An expression system contains a gene encoding a particular protein; a nucleic acid sequence encoding a signal peptide which directs secretion of the correctly processed protein into the growth medium; and a promoter capable of directing transcription of mRNA, which encodes the protein. As is known to those skilled in the art, expression systems would include additional nucleic acid sequences for termination of transcription and initiation and termination of translation.

In the preferred embodiment, the gene contained within an expression system encodes the protein human GM-CSF (Lee et al., 1985; Wang et al., 1985). The GM-CSF gene, specifically the one represented by the DNA sequence in FIG. 1, is a synthetic DNA which was created following the codon usage of Streptomyces; that is, codons with C or G in the third position (Bibb et al., 1985). The gene could be the natural cDNA sequence for GM-CSF, or any other DNA sequence encoding GM-CSF, with either Streptomyces codon usage, or any other biased or completely random codon usage. The gene could encode a biologically active derivative of GM-CSF in which one or more amino acids are substituted, inserted, or deleted in the natural amino acid sequence.

The heterologous gene contained within an expression system could be natural cDNA or a synthetic DNA sequence encoding another useful protein. The particular protein encoded by the recombinant DNA sequence may include eukaryotic secretory enzymes, such as chymosin, chymotrypsin, trypsins, amylases, ligninases, elastases, lipases, and cellulases; prokaryotic secretory enzymes, such as glucose isomerase, amylases, lipases, pectinases, cellulases, proteinases, oxidases, ligninases; enzyme inhibitors, such as hirudin, B-lactamase inhibitor, and alpha 1-antitrypsin; metalloenzymes, such as superoxide dismutase; blood factors, such as Factor VIII, Factor IX, tissue-type plasminogen activator and urokinase; hormones, such as proinsulin; lymphokines, such as beta and gamma-interferon, and interleukin-2; cytotoxins, such as tumour necrosis factor, lymphotoxin, and interleukin-1; growth factors, such as nerve growth factors, epidermal growth factors, transforming growth factor, platelet-derived growth factors, and fibroblast growth factors; other colony stimulating factors, such as interleukin-3 and granulocyte colony stimulating factor; immunoglobulin-related molecules, such as synthetic, designed, or engineered antibody molecules; cell receptors, such as cholesterol receptor; viral antigens, such as viral hemaglutinins, AIDS antigen and immunogen, hepatitis B antigen and immunogen, foot-and-mouth disease virus antigen and immunogen; bacterial surface effectors, such as protein A; toxins such as protein insecticides, algicides, fungicides, and biocides; and systemic proteins of medical importance, such as myocardial infarct protein (MIP), weight control factor (WCF), and caloric rate protein (CRP).

The gene could encode an inactive precursor (zymogen) of a biologically active protein, which could be processed into a active form either in vitro or in culture. The gene could encode a biologically active derivative of a useful protein in which one or more amino acids are substituted, inserted, or deleted in the natural amino acid sequence. In addition, the gene could encode a biologically active fusion protein of two or more useful proteins, or a hybrid of two or more homologous proteins, which could be created by exchanging single amino acids or blocks of amino acids from homologous positions within the sequences.

The signal sequence could encode any amino acid sequence which, when biosynthesized as an amino-terminal fusion protein, and is linked to a heterologous protein, is capable of directing the secretion of the heterologous protein with a correct amino terminus, into the medium. In the preferred embodiment, the signal peptide of *Streptomyces griseus* protease B (Canadian Application No. 542,648 filed on Jul. 21, 1987 by Cangene Corporation) is used to direct the secretion of GM-CSF: specifically, a 38-amino acid peptide of the sequence MRIKRTSNRSNAARRVRTTAVLAGLAAVAALAVPTANA. In another embodiment, the signal peptide which is used to direct the secretion of GM-CSF is a hybrid composed of the first 15 amino acids of the *S. griseus* protease B signal peptide joined at the amino terminus to amino acids 9 through 34 of the *Streptomyces plicatus* endo-B-N-acetylglucosaminidase H (endo H) signal peptide (Robbins et al., 1984): specifically, a 41-amino acid peptide of the sequence MRIKRTSNRSNAARRVRTAALALSAAAALVLGSTAASGASA. The secretion of GM-CSF could also be directed by the signal peptide of *S. plicatus* endo H, which is detailed in this invention; specifically a 34-amino acid peptide of the sequence MFTPVRRRVRTAALALSAAAALVLGSTAASGASA. The secretion could, in addition, be directed by another Streptomyces signal peptide: specifically, that of *S. griseus* protease A, *S. griseus* amylase, Streptomyces R61 DD-peptidase, or another Streptomyces signal peptide known in the art (Chang, 1987). Secretion could also be performed under the direction of a hybrid of the above signal peptides or one with a totally synthetic amino acid sequence. The signal peptide could be one from Gram-positive bacteria: specifically the signal peptide of *Bacillus subtilus* alkaline protease (apr), or another signal peptide of a Gram-positive bacteria known in the art (Chang, 1987). The signal peptide could also be from Gram-negative bacteria: specifically, the signal peptide of *Escherichia coli* outer membrane protein A, or another signal peptide of Gram-negative bacteria known in the art (Sjostrom et al., 1987). The signal peptide could also be a hybrid of two or more bacterial signal peptides. In one embodiment, the signal peptide which is used to direct the secretion of GM-CSF is a hybrid composed of the first 15 amino acids of the *S. griseus* protease B signal peptide joined at the amino terminus to amino acids 6 through 30 of the *B. subtilus* apr signal peptide: specifically a 40-amino acid peptide of the sequence MRIKRTSNRSNAARRVWISLLFALALIFTMAFGSTSSAQA. In addition to GM-CSF, other heterologous proteins could be secreted from Streptomyces with the signal peptides detailed in this invention or other bacterial signal peptides known in the art. Levels of secretion that could be achieved are greater than 1 ug/L of culture, but preferably greater than 1 mg/L.

The promoter directs the synthesis of an RNA encoding a fusion protein composed of the signal peptide joined to the amino terminus of the heterologous protein. The promoter permits the specific binding of and transcription by at least one type of Streptomyces RNA polymerase holoenzyme. In the Preferred embodiment, the promoter of the *Streptomyces fradiae* aminoglycoside phosphotransferase gene ("aph") (Thompson and Gray, 1983) is used to transcribe the mRNA encoding the signal peptide fused to GM-CSF. This promoter permits the binding of and transcription by at least one type of Streptomyces RNA polymerase holoenzyme. The promoter could be from another Streptomyces spp. including that of *Streptomyces erythreus* erythromycin E, *Streptomyces coelicolor* agarase, or any sequence of known or undetermined origin that has promoter activity as demonstrated by methods known in the art. The promoter may be a hybrid of more than one natural or completely synthetic promoter sequences. The promoter may be a natural or hybrid sequence in which one or more bases have been substituted, inserted or deleted to obtain a mutant version of the promoter with improved function. The mutation events may occur chemically or enzymatically, in either a random or site directed manner, and either in vitro or within a prokaryotic host cell.

The promoter may be either a single promoter with one transcription initiation site or a multiple promoter with two or more transcription initiation sites. In the preferred embodiment, the aph promoter is located on a DNA fragment which has two sites for initiation of transcription. Site 1 would begin transcription at the A of the translation initiator ATG, whereas site 2 would begin transcription 313 bases further upstream from site 1. In another embodiment, the aph promoter with only initiation site 1 is used to transcribe the mRNA encoding the signal peptide fused to GM-CSF. Each transcription initiation site of a multiple promoter may be recognized by the same or different type of RNA polymerase holoenzyme, and may be active at the same or different growth time or developmental state. The promoter with multiple transcription initiation sites may be a natural sequence or a hybrid sequence composed of more than one natural or synthetic single promoter sequences. The promoter, single or multiple, may be active at all times during the culturing (constitutive), or it may be regulated by the presence or absence of certain media components, metabolites, or chemical agents. In addition, the promoter may be regulated by changing the temperature or chemical environment of the culture.

In the preferred embodiment, the aph promoter is joined to a nucleic acid sequence encoding a signal peptide, which is joined in-frame to a nucleic acid sequence encoding a protein, in particular GM-CSF. The aph promoter was joined to synthetic oligonucleotides, which encode a signal peptide, by using an NcoI restriction endonuclease site. This site contains the natural initiator ATG of the aph gene, which in this configuration represents the amino-terminal methionine of the signal peptide. A DNA sequence which is complementary to the 3' end of the 18S ribosomal RNA of *Streptomyces lividans* may be included at this NcoI site to augment the initiation of translation. For convenience, a PstI or NsiI site is positioned at the signal processing site to join a DNA sequence encoding the protein to be secreted. The GCA codon in the PstI or NsiI site represents the alanine at the carboxy terminus of the signal peptide. In the preferred embodiment, the DNA sequences are configured so that the carboxy terminus of the encoded signal peptide is fused directly to the amino terminus of the encoded protein of interest. An additional peptide encoding sequence may be inserted at the PstI or NsiI site to facilitate secretion or processing of the signal peptide. The resulting protein with an amino-terminal extension may be removed either in culture by a natural process or in vitro by known chemical or enzymatic methods.

It is contemplated that the signal peptides which are described in this invention, specifically, the 38-amino acid protease B signal peptide, the 34-amino acid endo H signal peptide, the 41-amino acid protease B-endo H hybrid signal peptide, and the 40-amino acid protease B-apr hybrid signal peptide, may be used with expression systems other than those described in this invention, for the secretion of heterologous proteins. The signal peptides which are described in this invention may be used in other expression systems, particularly expression systems for other gram positive bacteria (Chang 1987), specifically expression systems for *Bacillus subtilis* and *Staphylococcus aureus*. It is also contemplated that a fusion protein may be synthesized by a natural process in a bacterial host other than Streptomyces, and from an expression system, which includes a DNA segment which functions as a promoter, linked to a DNA segment which encodes one of the signal peptides described in this invention, linked to a DNA segment which encodes a heterologous protein. The fusion protein would have at its amino terminus one of the signal peptides which are described in this invention, and at its carboxy terminus a heterologous protein which may be GM-CSF. The carboxy terminus of the signal peptide may be joined directly to the amino terminus of the heterologous protein to form the fusion protein. The fusion protein would be useful for secretion of the heterologous protein in the bacterial host.

The genetic expression system, consisting of a promoter, a nucleic acid sequence encoding a signal peptide, and a nucleic acid sequence encoding the particular protein of interest, is situated in a DNA vector which is capable of transformation and replication in Streptomyces. This vector could contain a derivative of a naturally occurring plasmid of Streptomyces including pIJ101, pSLP1.2, pSCP2*, or a naturally occurring phage of Streptomyces including ØC31, or any non-streptomycete plasmid or bacteriophage which is capable of replication in Streptomyces. The vector may be capable of autonomous replication in the host organism, or may require integration into the chromosome or a large extrachromosomal element of the host organism. In the latter case, the vector would contain appropriate nucleic acid sequences capable of facilitating in vivo recombination with either a specific or undefined DNA sequence in the host genome. These sequences could include a plasmid or phage att site, a recombinogenic sequence of a transposable element, or any sequence with sufficient homology with a segment of the host genome to promote integration. It is contemplated that DNA segments which are naturally amplified in the genome of Streptomyces, specifically the 5.7-kb amplifiable unit of DNA (AUD) of *Streptomyces coelicolor*, may be included in the vector, and used to obtain multiple-copy integration of the genetic expression system. The vector also contains an appropriate gene to provide selection for the transformed strain of the host organism, both during transformation and subsequent culturing of the transformant. This selection marker could provide resistance to an antibiotic such as thiostrepton, kanamycin, viomycin, hygromycin, or it could complement an auxotrophic or conditional lethal mutant of the host organism.

In the preferred embodiment, the plasmid pIJ680 was adapted for service as a vector according to the modifications outlined in FIG. 2. In the first stage, the 2354-base pair PvuII fragment of the *E. coli* plasmid pUC8 was introduced into the PstI site at position 3390 (site number 16) of pIJ680 (Hopwood et al, 1985). The blunt-ended PvuII fragment was joined to the -TGCA 3' end of the PstI site with a synthetic adaptor as shown in FIG. 2. Vectors with the *E. coli* plasmid inserted at the PstI site are capable of replication in either *E. coli*, under ampicillin selection, or Streptomyces with selection for thiostrepton resistance. It will be appreciated that the *E. coli* plasmid portion of the vector only facilitates assembly of the expression systems in the vector and is not required once the completed plasmid is ready for transformation of Streptomyces. For example, the *E. coli* plasmid segment could be removed prior to transforming Streptomyces by partial digestion with ClaI followed by recircularization of the vector with DNA ligase.

In the second stage, the promoter and coding region of the aph gene was replaced with a synthetic DNA sequence to facilitate future constructions. This involved the alteration of the SacII site at position 4883 (site number 32) of pIJ680 (Hopwood et al, 1985) by ligating a synthetic BglII linker GAGATCTC to the second C in the CCGCGG SacII site. In one embodiment, the BglII site is converted to a BamHI site by ligating a synthetic linker CGGATCCG to the C in the AGATCT BglII site, resulting in the vector pSS2. In another embodiment, the XbaI site is converted to a Hind III site by ligating a synthetic linker CAAGCTTG to the G in the TCTAGA XbaI site.

The BamHI-XbaI fragment of pSS2 could be replaced with an expression system composed of a promoter, a nucleic acid sequence encoding a signal peptide, and a nucleic acid sequence encoding the particular protein of interest. Although the restriction sites BamHI, and XbaI were chosen for convenience, it should be understood that any other restriction site could be used in place of or in addition to these for joining the genetic expression system to the vector. The expression system could be inserted between the BamHI and XbaI sites in either direction, although the preferred orientation would allow transcription in a counter-clockwise direction, as defined by FIG. 2. This would allow utilization of the aph transcription terminator which is adjacent the XbaI site [located between positions 3955 (site 21) and 3843 (site 19) of the original pIJ680 (Hopwood et al, 1985)]. However, any transcription terminator known in the art could be used in place of, or in addition to, the one for aph. The pSS2 vector may have sites for initiation of transcription which are not utilized for expression of the heterologous gene.

Expression vectors can be constructed by inserting various genetic expression systems into the pSS2 vector. According to one embodiment, an expression system pAPO.GMCSF (FIG. 3) contains an aph promoter joined to a nucleic acid sequence encoding the protease B signal peptide which is joined to a nucleic acid sequence encoding GM-CSF. According to another embodiment, an expression system pAEO GMCSF (FIG.

4) contains an aph promoter joined to a nucleic acid sequence encoding the protease B-endo H hybrid signal peptide which is joined to a replaceable nucleic acid sequence encoding GM-CSF. In another embodiment, an expression system pAPO.G (FIG. 5) contains an aph promoter joined to a nucleic acid sequence encoding the protease B signal peptide which is joined to a replaceable nucleic acid sequence. In a further embodiment, an expression system PAP0.H was constructed from pAP0.G by the insertion of a synthetic DNA (CTAGCAAGCTTG) into the XbaI site. An expression system pAEO.SX (FIG. 6) contains an aph promoter joined to a nucleic acid sequence encoding the protease B-endo H hybrid signal peptide which is joined to a replaceable nucleic acid sequence. In a further embodiment, an expression system pAE0.SH was constructed from pAE0.SX by the insertion of a synthetic DNA (CTAGCAAGCTTG) into the XbaI site. Another alternative is an expression system pAPO.SX (FIG. 7) which contains an aph promoter joined to a nucleic acid sequence encoding the protease B signal peptide which is joined to a replaceable nucleic acid sequence.

The BamHI-MluI fragments in all the expression vectors can be replaced with a DNA fragment containing a different promoter and/or encoded signal peptide amino terminus. Also, either the MluI-PstI fragment of pAEO.GMCSF, pAEO.SX, pAEO.SH, or pAPO.SX; or the MluI-NsiI fragment of pAPO.G, or pAPO.H can be replaced with a DNA fragment encoding an alternative signal peptide. Similarly, either the PstI-Hind III fragment of pAEO.GMCSF or pAEO.SH; or the PstI-XbaI fragment of pAEO.SX or pAPO.SX; or the NsiI-HindIII fragment of pAPO.H; or the NsiI-XbaI fragment of pAPO.G can be replaced with another DNA fragment encoding a protein.

Preferred embodiments of the invention are exemplified in the following procedures. Such procedures and results are by way of example and are not intended to be in any way limiting to the scope of the appended claims.

PREPARATIONS

Strains and Plasmids

*Streptomyces lividans* 66 (Bibb et al., 1980), and plasmids pIJ61 (disclosed by Thompson et al., 1982, and can be isolated from *S. lividans* 66/TC73) and pIJ680 (disclosed by Hopwood et al., 1985, and can be isolated from *S. lividans* TK24/TK425) were from the John Innes Institute. *E. coli* strain HB101 (ATCC 33694) was used for all transformations. Plasmids pUC8 (Vieira and Messing, 1982), and pUC18 and pUC19 (Norrander et al., 1983) were purchased from Bethesda Research Laboratories. Plasmid pUC680T was deposited with the American Type Culture Collection on Jun. 28, 1988 under accession number 40466.

Materials

Oligonucleotides were synthesized using an Applied Biosystems 380A DNA synthesizer. Columns, phosphoramidites, and reagents used for oligonucleotide synthesis were obtained from Applied Biosystems, Inc. through Technical Marketing Associates. Oligonucleotides were purified by polyacrylamide gel electrophoresis followed by DEAE cellulose chromatography. Enzymes for digesting and modifying DNA were purchased from New England Biolabs, and used according to the supplier's recommendations. Radioisotopes [α-32P]dATP (3000 Ci/mmol) and [γ-32P]ATP (3000 Ci/mmol) were from Amersham. Thiostrepton was donated by Squibb Corporation of N.Y.

Isolation of DNA

Plasmid DNA of transformed *S. lividans* was prepared by an alkaline lysis procedure (Hopwood et al., 1985). *E. coli* transformants were grown on YT medium (Miller, 1972) containing 50 ug/ml ampicillin. Plasmid DNA from *E. coli* was purified by a rapid boiling method (Holmes & Quigley, 1981). DNA fragments and vectors used for all constructions were separated by electrophoresis on low melting point agarose, and purified from the molten agarose by phenol extraction and ethanol precipitation (Maniatis et al., 1982).

DNA Sequencing

Plasmid DNA, which was purified by HPLC (Edwardson et al., 1986), was sequenced by using a modification (Hattori et al., 1985) of the dideoxy method (Sanger et al., 1977). When necessary, subclones were prepared in the M13 bacteriophages mp18 and mp19 (Norrander et al., 1983) and the dideoxy sequencing reactions were run using the −20 universal primer (New England Biolabs). In some areas of strong secondary structure, compressions and polymerase failure necessitated the us of deazaguanosine (Mizusana et al., 1986) (Boehringer Mannheim) analogs in the dideoxy reactions to clarify the sequence. The sequences were compiled with the software of DNASTAR ™ (Doggette and Blattner, 1985).

EXAMPLE 1

Construction of pUC680T

The Streptomyces plasmid pIJ680 (1-2 ug) was linearized by partial digestion with 1.2 units of PstI for 4 min. The 5.3-kb PstI DNA fragments representing the linearized pIJ680 plasmid were mixed with the *E. coli* plasmid pUC8 which had been digested with PstI and calf intestinal alkaline phosphatase. The mixture was then ligated with T4 DNA ligase and transformed into *E. coli*. The transformants were screened by analysis of the plasmid DNA for the correct recombinant. One plasmid, pUC680, had the pUC8 plasmid inserted into the PstI site at position 3390 (site number 16) of pIJ680.

A subclone of pIJ680 was constructed to facilitate the replacement of the aph promoter and coding region. This subclone, pCM680B, contains the 0.41-kb SacII-XhoI DNA fragment of pIJ680 (Hopwood et al, 1985) from positions 4883 to 5290 (between site numbers 32 and 1). The SacII site has been changed to BglII by ligation of the synthetic linkers GAGATCTC to the SacII site which had been made blunt-ended with the Klenow fragment of DNA polymerase I. The newly created BglII site is adjacent to 0.92 kb of synthetic DNA which ends with an XbaI site.

The 1.33-kb XbaI-XhoI DNA fragment of pCM680B, which contains the synthetic DNA fragment joined to the pIJ680 subclone, was mixed with the 6.6-kb XbaI-XhoI DNA fragment of pUC680, which contains the *E. coli* vector. The mixture was ligated with T4 DNA ligase and transformed into *E. coli*. The resultant plasmid pUC680T was found by analyzing the plasmid DNA of the transformants. The plasmid pUC680T was deposited with the American Type Culture Collection on Jun. 28, 1988 under accession number 40466.

EXAMPLE 2

Construction of pSS2

The 2.36-kb PvuII fragment of pUC8 was ligated to Phosphorylated ClaI linkers (New England Biolabs) of the sequence CATCGATG, using T4 DNA ligase. The ligation reaction was terminated by heating at 65° C. and digested with NsiI, which utilizes the sites generated by the ligation of consecutive linkers. The 2.36-kb NsiI fragment was isolated and mixed with the 5.3-kb PstI fragment of pUC680T. The mixture was ligated using T4 DNA ligase in the presence of NsiI and PstI. The ligation reaction was terminated by heating at 65° C., digested with NsiI, and transformed into E. coli. The plasmid pSS1, which was found by analyzing plasmid DNA of the transformants, contained the E. coli plasmid segment inserted into the former PstI site in the orientation shown in FIG. 2.

The unique BglII site of pSS1 was changed to BamHI to facilitate exchange of promoter sequences. The Plasmid pSS1 was digested with BglII and the ends of the linearized plasmid were filled in with the Klenow fragment of DNA polymerase I. The blunt-ended DNA fragment was then ligated to phosphorylated BamHI linkers (New England Biolabs) of the sequence CGGATCCG, using T4 DNA ligase. The ligation reaction was terminated by heating at 65° C., and digested with BamHI. The purified linear plasmid with BamHI ends was then recircularized by using T4 DNA ligase and transformed into E. coli. The resultant plasmid, pSS2, with a unique BamHI site replacing the original BglII site, was found by analyzing the plasmid DNA of the transformants.

EXAMPLE 3

Subcloning a DNA Fragment Containing the aph Promoter

A 2.1-kb EcoRV-NcoI fragment of the Streptomyces plasmid pIJ61 was digested with Sau3AI and ligated into the BamHI and NcoI sites of an appropriate vector. Among the recombinants was found the subclone of pIJ61, pAPH.4, which contained the 0.40-kb Sau3AI-NcoI fragment with a sequence corresponding to the aph promoter (FIG. 8). The NcoI site contains the initiator ATG of the aph gene.

EXAMPLE 4

Subcloning the DNA Fragment Containing the Protease B Promoter and Signal Peptide A subclone of the protease B gene was prepared from the 1.4-kb BssHII fragment of plasmid containing the 2.8-kb BglII fragment which contained the protease B gene (Canadian Application No. 542,648 filed on Jul. 21, 1987 by Cangene Corporation). The ends of the BssHII fragment were filled in by using the Klenow fragment of DNA polymerase I, and then ligated to phosphorylated BamHI linkers, following the teaching of Example 2. The resulting 1.4-kb fragment with BamHI ends was ligated into a pUC8 vector which had been digested with BamHI and treated with alkaline phosphatase. The resulting plasmid pSPRB1.4 contained the entire protease B gene.

The plasmid pUC8 was adapted for further subcloning by the ligation of two annealed oligonucleotides, GGCCTCGTCTAGA and AAGCTTCTAGACGAGGCCTGCA, into the PstI and HindIII sites, resulting in the plasmid pUC.PXH. The plasmid pSPRB1.4 was digested with PvuII and ligated to Phosphorylated PstI linkers (New England Biolabs) of the sequence GCTGCAGC, using T4 DNA ligase. The ligation reaction was terminated by heating at 65° C., and digested with PstI and BamHI. The 0.49-kb BamHI-PstI fragment was purified and then ligated into the BamHI and PstI sites of the pUC.PXH vector. The resulting plasmid, pPP1, contained the promoter, signal peptide and the first 10 amino acids of the propeptide, all of the protease B gene.

EXAMPLE 5

Construction of Expression Systems Using the Protease B Signal Peptide

Adaptation of the protease B signal for heterologous protein secretion involved the use of two synthetic oligonucleotides, a 42-mer and a 50-mer, encoding the carboxy-terminal 9 amino acids of the protease B signal peptide and the amino-terminal 8 amino acids of human growth hormone (FIG. 10). The synthetic oligonucleotides were joined in a 3-way ligation to a 0.44-kb BamHI-HaeII fragment of the protease B subclone pPP1 (FIG. 9), and the vector fragment of pSS2 which was digested with BamHI and XbaI. The resulting plasmid, pPP0.G, had a 0.46-kb BamHI-NsiI segment containing the protease B promoter and signal peptide. The NsiI site contained a GCA codon for the alanine residue immediately preceding the processing site (−1 position).

The signal peptide of protease B was adapted for expression from the aph promoter by using two synthetic 43-mers encoding the first 15 amino acids of the protease signal peptide (FIG. 11). The synthetic oligonucleotides were joined in a 3-way ligation to the 0.40-kb BamHI-NcoI fragment containing the aph promoter (FIG. 8), and the BamHI-MluI vector fragment of pPP0.G, following the teaching of this example. The resulting expression vector, pAP0.G, had a 0.51-kb BamHI-NsiI segment containing the aph promoter joined to a sequence encoding the protease B signal peptide, and a 0.03-kb NsiI-XbaI segment containing a replaceable sequence encoding a protein (FIG. 5).

EXAMPLE 6

Construction of Alternative Expression Systems Using the Protease B Signal Peptide A plasmid pPCM, containing a 1.1-kb PstI-XbaI fragment which encodes a protein, was digested with PstI and XbaI, and the 1.1-kb fragment was ligated into the PstI and XbaI sites of the pPP1 vector. The resulting plasmid, pPP1.PCM, contained in a single vector the 0.49-kb BamHI-PstI fragment of pPP1 joined to the 1.1-kb PstI-XbaI fragment of pPCM.

Further adaptation of protease B signal for heterologous protein secretion involved the use of two synthetic 26-mer oligonucleotides, encoding the carboxy-terminal 9 amino acids or the protease B signal peptide (FIG. 12). The synthetic oligonucleotides were joined in a 3-way ligation to the 0.44-kb BamHI-HaeII fragment of pPP1 and the vector fragment of pPP1.PCM which was digested with BamHI and PstI. The resulting plasmid pPP0.PCM had a 0.46-kb BamHI-PstI segment containing the protease B promoter and signal peptide. The PstI site contained a GCA codon for an alanine residue immediately following the processing site (+1 position).

The 1.6-kb BamHI-XbaI fragment of pPPO.PCM was then ligated to the BamHI-XbaI vector fragment of pSS2. The resulting plasmid, pPPO-PCM/S2, contained the protease B promoter and signal peptide, joined to a synthetic DNA segment encoding a protein, all in the pSS2 vector.

The signal peptide of protease B in the pPPO.PCM/S2 construction was adapted for expression from the aph promoter by following the teaching of Example 5. The 43-mer oligonucleotides encoding the first 15 amino acids of the protease B signal peptide were joined in a 3-way ligation to the 0.40-kb BamHI-NcoI fragment containing the aph promoter, and the BamHI-MluI vector fragment of pPPO.PCM. The resulting expression vector, pAPO.PCM, had a 0.51-kb BamHI-PstI segment containing the aph promoter joined to a sequence encoding the protease B signal peptide.

For convenience, the DNA segment encoding the protein in the vector pAPO.PCM was shortened by deleting the 0.8-kb SacI-XbaI fragment. The vector pAPO.PCM was digested with SacI and XbaI, and the vector fragment was recircularized by ligation to the synthetic oligonucleotide CTAGAGCT. The resulting expression vector pAPO.SX (FIG. 7), which retains sites for both SacI and XbaI, has a 0.51-kb BamHI-PstI segment containing the aph promoter joined to a sequence encoding the protease B signal peptide, and a 0.32-kb PstI-XbaI (or PstI-SacI) segment containing a replaceable sequence encoding a protein.

EXAMPLE 7

Construction of Expression Systems Using the Protease B- Endo H Hybrid Signal Peptide A synthetic DNA sequence was designed using the amino acid sequence of the endo H signal peptide and the codon usage for Streptomyces. The synthetic sequence and its complement were divided into six oligonucleotides. The first two of these, S1.END and S2.END, were joined to the aph promoter (see Example 11). The next four of these, S3.END through S6.END, encoded the remaining 27 amino acids of the endo H signal peptide (FIG. 13). The oligonucleotides S4.END and S5.END (2 ug each), were phosphorylated separately in 20-ul reactions containing 10 mM TrisHCl (pH 7.5), 10 mM MgCl2, 5 mM DTT, 0.5 mM ATP and 5 units T4 polynucleotide kinase, at 37° C. for 30 min. The phosphorylated oligonucleotides (10 ul of each) were mixed with 1 ug each of unphosphorylated S3.END and S6.END, and 3 ul 500 mM TrisHCl (pH 7.8)-100 mM MgCl2, in a final volume of 31 ul. Annealing of the oligonucleotides was at 90° C. for 10 min, followed by slow cooling to room temperature for 12 to 16 h. The annealed oligonucleotides (15 ul) were ligated together in a 200-ul reaction containing 50 mM TrisHCl (pH 7.8), 10 mM MgCl2, 1 mM ATP, and 1600 Units T4 DNA ligase, at 8° C. for 4 h. The completed synthetic gene segment encoding the endo H signal peptide was then ligated to the MluI and PstI sites of the expression vector pAPO.SX, which contained the aph promoter, the protease B signal peptide, and a replaceable synthetic DNA segment (FIG. 7). This joined the amino-terminal 15 amino acids of the protease B signal to the carboxy-terminal 26 amino acids of the endo H signal, to form a protease B-endo H hybrid signal peptide. The PstI site contains a GCA codon for the alanine at the −1 position of the signal peptide. The resulting expression vector, pAEO.SX, had a 0.52-kb BamHI-PstI fragment containing the aph promoter joined to a sequence encoding the protease B-endo H hybrid signal peptide, and a 0.32-kb PstI-XbaI (or PstI-SacI) segment containing a replaceable sequence encoding a protein (FIG. 6).

EXAMPLE 8

Construction of a Synthetic Gene Encoding GM-CSF

A synthetic DNA sequence was designed by back translation of the GM-CSF amino acid sequence using a codon selection for Streptomyces. This DNA sequence and its reverse complement were used for the synthesis of 16 oligonucleotides, which were annealed and ligated together, following the teaching of Example 7. The completed 0.48-kb synthetic GM-CSF gene (FIG. 1) was then ligated into the PstI and XbaI sites of pUC18 and used to transform E. coli. The PstI site contained a GCA codon for the alanine at the −1 position, which is compatible with the protease B and endo H expression systems. After screening the transformants by restriction analysis of the plasmid DNA, the synthetic GM-CSF gene was determined to be authentic by DNA sequence analysis.

EXAMPLE 9

Construction of Expression Vectors For GM-CSF Using the Protease B Signal Peptide The XbaI site of PAP0.G was converted to a HindIII site to facilitate the insertion of the synthetic GM-CSF gene. The vector pAP0.G was digested with XbaI, and the resulting ends of the linear vector were filled in by using the Klenow fragment of DNA polymerase I, and then ligated to phosphorylated HindIII linkers (New England Biolabs) of the sequence CAAGCTTG, using T4 DNA ligase. The reaction was terminated by heating at 65° C., and digested with HindIII. The purified linear plasmid with HindIII ends was then recircularized by using T4 DNA ligase. The resulting expression vector, pAP0.H, has a 0.51-kb BamHI-NsiI segment containing the aph promoter joined to a sequence encoding the protease B signal peptide, and a 0.03-kb NsiI-HindIII segment containing a replaceable sequence encoding a protein.

The 0.48-kb PstI-XbaI fragment of pUC.GMCSF, containing the GM-CSF gene was ligated to the BamHI-PstI vector fragment of pAPO.G, containing the aph promoter and encoding the protease B signal peptide, by using T4 DNA ligase. In the resulting expression vector, pAP0.GMCSF, the carboxy terminus of the encoded signal peptide is fused directly to the amino terminus of the encoded GM-CSF protein.

EXAMPLE 10

Construction of Expression Vectors For GM-CSF Using the Protease B-endo H Hybrid Signal Peptide The XbaI site of pAE0.SX was converted to a HindIII site, by following the teaching of Example 9. The resulting expression vector, pAE0.SH, has a 0.52-kb BamHI-PstI segment containing the aph promoter joined to a sequence encoding the protease B-endo H hybrid signal peptide, and a 0.32-kb PstI-HindIII (or PstI-SacI) segment containing a replaceable sequence encoding a protein.

The 0.48-kb PstI-Hind III of pUC.GMCSF, containing the GM-CSF gene, was ligated to the PstI-Hind III vector fragment of pAE0.SH, containing the aph promoter and encoding the protease B - endo H hybrid signal peptide. In the resulting expression vector, pAE0.GMCSF, the carboxy terminus of the encoded signal peptide is fused directly to the amino terminus of the encoded GM-CSF protein.

EXAMPLE 11

Construction Of Expression Systems Using the Endo H Signal Peptide

The amino terminus of the signal peptide in pAEO.GMCSF, was changed from protease B to endo H by replacing the 0.44-kb BamHI-MluI fragment, in a 3-way ligation, with the 0.40-kb BamHI-NcoI fragment of pAPH.4 and the annealed oligonucleotides S1.END (CATGTTCACTCCCGTTCGGAGA) and S2.END (CGCGTCTCCGAACCGGAGTGAA) following the teaching of Example 5. The resulting expression vector, pAEO-1.GMCSF, had a 0.50-kb BamHI-PstI fragment containing the aph promoter joined to a sequence encoding the endo H signal peptide.

EXAMPLE 12

Construction of Expression Vectors For GM-CSF Using the Protease B-apr Hybrid Signal Peptide A synthetic DNA sequence was designed using the amino acid sequence of the apr signal peptide and the codon usage for Streptomyces. Construction of the protease B-apr hybrid signal peptide expression vector involved the use of two synthetic oligonucleotides, a 81-mer and a 73-mer, encoding amino acid 15 of the protease B signal peptide and the carboxy terminal 25 amino acids of the apr signal peptide (FIG. 14). The synthetic oligonucleotides were annealed and then ligated to the MluI and PstI sites of the expression vector pAEO.SH (FIG. 6). The resulting plasmid, pAapr.SH, contained the aph promoter, a sequence encoding the protease B-apr hybrid signal peptide, and a replaceable synthetic DNA segment. The protease B-apr hybrid signal peptide contains the amino terminal 15 amino acids of the protease B signal peptide joined to the carboxy terminal 25 amino acids of the apr signal peptide.

The synthetic GM-CSF gene was adapted to the pAapr.SH expression vector by using two synthetic oligonucleotides, a 21-mer (CCCGCCCGGTCGCCCTCGCCG) and a 29-mer (TCGACGGCGAGGGCGACCGGGCGGGTGCA), encoding the amino terminal 9 amino acids of GM-CSF. The synthetic oligonucleotides were annealed and then joined in a 3-way ligation to a 0.36-kb SalI-HindIII fragment of pUC.GMCSF (FIG. 1) and the vector fragment of pAapr.SH which had been digested with PstI and HindIII. In the resulting expression vector, pAapr.GMCSF, the carboxy terminus of the encoded signal peptide is fused directly to the amino terminus of the encoded GM-CSF protein.

EXAMPLE 13

Construction of Expression Vectors For GM-CSF Using an Aph Promoter With a Single Transcription Initiation Site The expression vector pAPO.GMCSF was digested with SacII, and the resulting fragments were made blunt-ended by treatment with the Klenow fragment of DNA polymerase I. The blunt-ended SacII fragments were then ligated to phosphorylated BamHI linkers following the teaching of Example 2. The ligation mixture was digested with BamHI and HindIII, and the 0.62-kb fragment was purified. The 0.62-kb BamHI-HindIII fragment, was then ligated to the vector fragment of pAPO.H which had been digested with BamHI and HindIII. The resulting expression vector, pA*-PO.GMCSF, had the 0.12-kb aph promoter segment joined to a sequence encoding the protease B signal peptide which was joined to a sequence encoding GM-CSF.

EXAMPLE 14

Transformation of S. Lividans With GM-CSF Expression Systems

Protoplasts of S. lividans 66 that were used for transformations. Cultures of S. lividans 66 were grown in YEME medium (Hopwood et al., 1985) including 0.5% glycine, at 30° C. for 40 h. Protoplasts were prepared from the harvested mycelium by treatment with lysozyme and purified by filtration through Miracloth (Calbiochem Hoechst) as described (Hopwood et al., 1985). Protoplasts ($4 \times 10^9$) were transformed with plasmid DNA of the expression vectors (1 ug) and spread onto R2YE plates as described (Hopwood et al., 1985). After incubating at 30° C. for 22 h, the plates were overlayed with Soft Nutrient Agar, containing thiostrepton (30 ug/ml), and allowed to incubate at 30° C. until sporulation occurred.

EXAMPLE 15

Growth of S. Lividans Transformants

Ten colonies of S. lividans 66, which had been transformed with a GM-CSF expression vector, were inoculated into 15 ml of LB medium, containing thiostrepton (5 ug/ml), and grown at 32° C. for 65 h. The culture was dispersed by using a 15-ml tissue homogenizer (Tenbroeck-Bellco) and used as inoculum for a second culture. A 2-1 baffled shake flask, containing 200 ml LB medium, plus thiostrepton (5 ug/ml), was inoculated to A600 of 0.2 and incubated at 32° C. for 2–4 days in an environment shaker (240 rpm). Two 10-ml aliquots were removed from the culture at suitable time points between 0 and 96 h of growth. The mycelia, which was used for dry weight determination, were removed by centrifugation at 4000 rpm for 10 min. in a clinical centrifuge at 4° C. The supernatant fractions which contained secreted proteins including GM-CSF, were frozen at −20° C. prior to analysis.

EXAMPLE 16

Monitoring Secretion of GM-CSF

The supernatant fraction described in Example 15 which contain secreted proteins including GM-CSF were analyzed by polyacrylamide gel electrophoresis and the protein or proteins of interest visualized either by staining with a protein specific stain or by analysis by Western blotting. 1.5 ml aliquots of the culture supernatants were concentrated by addition of a 50% (w/v) solution (on ice) of trichloroacetic acid (TCA) to a final concentration of 10% (w/v) and incubation of the resulting mixture at approximately 4° C. for approximately 15–30 minutes. The precipitate which forms, which includes secreted proteins including GM-CSF, was collected by centrifugation in an Eppendorf centrifuge at maximum speed for 5 minutes at room temperature. The precipitated samples were prepared for electrophoresis according to the method described by Laemmli, (1970), including a modification to adjust the pH of the resuspended TCA precipitates to that of the sample buffer by the addition of 2N NaOH. Polyacrylamide gels (15% acrylamide) were run according to the procedure described by Laemmli, (1970.)

The profile of proteins separated by the procedure described above was visualized by staining with Coomassie Brilliant Blue (FIG. 15a). A novel protein band is present in the cells containing the GM-CSF gene which runs with an apparent molecular weight of approximately 15,500 Daltons when compared to Pharmacia Low Molecular Weight standards (indicated by arrows in FIG. 15). This band was identified as GM-CSF by its cross-reaction with a monoclonal antibody against GM-CSF. This analysis was performed by Western blotting of the proteins separated by gel electrophoresis (FIG. 15b) where the novel protein band found in the GM-CSF transformants cross-reacts with the antibody raised against GM-CSF. Western blotting was performed according to the procedure of Towbin et al., (1979) as modified by Burnette, (1981).

Quantitation of the level of secretion of GM-CSF was performed by scanning both Coomassie Brilliant Blue stained gels and Western blots, (Table I). Total protein in the supernatants was determined by Bio-Rad protein assay.

The levels of secreted GM-CSF are highest in the S. lividans containing pAPO.GMCSF (lanes 9-10). Slightly lower levels of secreted GM-CSF were observed for pA*PO.GMCSF (lanes 11-12), which contained the aph promoter with the single initiation site. Substitution of the carboxy-terminal 23 amino acids of the protease B signal peptide in pAPO.GMCSF (lanes 5-6), with the carboxy-terminal 26 amino acids of the endo H signal peptide in pAEO.GMCSF (lanes 1-2), or with the carboxy-terminal 25 amino acids of the aph signal peptide in pAapr.GMCSF, resulted in approximately 3 fold lower levels of secreted GM-CSF. However, the levels of secreted GM-CSF were higher by using the protease B-endo H hybrid signal peptide of pAEO.GMCSF than by using the endo H signal peptide of pAEO-1.GMCSF (lanes 7-8), indicating than the hybrid signal peptide is better than the natural signal peptide.

EXAMPLE 17

Testing Biological Activity of GM-CSF

The biological activity for secreted GM-CSF was determined by the methylcellulose colony stimulating assay whereby the cells are scored for their ability to stimulate the growth of colonies in soft agar. In summary non-adherent bone marrow cells for the hematopoietic colony-stimulating activity assay were prepared from samples obtained from healthy adult human subjects as described by Gregory and Eaves (1977). For assays the cells were plated at a final concentration of approximately $5 \times 10^4$ cells/ml. The culture medium contained 0.8% methylcellulose, 30% fetal Calf Serum (Flow), 1% deionized bovine serum albumin (BSA, Sigma Chemical Co., St. Louis), 0.1 mM 2-mercaptoethanol and alpha medium as described by Coulombel et al (1983) and Cashman et al (1985). Cells were incubated in the presence of the media containing the growth factor for a time period of generally 7-14 days at 37° C. in a fully humidified atmosphere of 5% $CO_2$ in air. Colonies were scored in situ under an inverted microscope.

The analysis of biological activity was performed for both pAPO.GMCSF and pAEO.GMCSF (Table II) and in both cases there was demonstration of the significant stimulation of Granulocyte/Macrophage type colonies with a low level of stimulation of large Erythroid/Mixed colonies in the same ratio at found with 10% human leucocyte conditioned media (containing human GM-CSF).

TABLE I

| Expression of GM-CSF from different constructs transformed in S. lividans 66. | | | |
|---|---|---|---|
| CONSTRUCT | TIME (h) | DRY WT (g/l) | GM-CSF (mg/l) |
| pAPO.GMCSF | 28 | 1.9 | 14.5 |
| pAEO.GMCSF | 28 | 2.0 | 4.0 |
| pAEO-1.GMCSF | 28 | 2.2 | <0.1 |
| pAapr.GMCSF | 28 | 2.2 | 4.0 |
| pA*PO.GMCSF | 28 | 2.2 | 12.0 |

TABLE II

| Colony stimulating activity of supernatants of pAPO.GMCSF and pAEO.GMCSF and also a negative control sample transformed with a different heterologous gene. | | | |
|---|---|---|---|
| | | # of Colonies Stimulated | |
| CONSTRUCT | TIME | Large Erythroid/ Mixed | Granulocyte/ Macrophage |
| pAPO.GMCSF | 22 | 14 | 118 |
| pAPO.GMCSF | 29 | 13 | 124 |
| pAEO.GMCSF | 22 | 16 | 113 |
| pAEO.GMCSF | 29 | 9 | 106 |
| pAPO.CONTROL | 22 | 0 | 5 |
| pAPO.CONTROL | 29 | 0 | 3 |
| AUTHENTIC HUMAN GM-CSF | N/A* | 22 | 120 |

*Not applicable.

EXAMPLE 18

Purification of GM-CSF

GM-CSF was purified in small quantities by elution of the GM-CSF band from a polyacrylamide gel. 10 ml of supernatant proteins were harvested at approximately 24 h of growth and the mycelia removed by centrifugation at 4000 rpm for 10 min. in a clinical centrifuge at 4° C. The supernatant proteins which include GM-CSF were concentrated according to the teaching of Example 16 and separated on a 15% polyacrylamide gel run according to the procedure of Laemmli (1970) with the modifications for the sample preparation and running of the gel described by Hunkapiller, et al., (1983). The GM-CSF protein band was isolated by the gel elution procedure described by Hunkapiller et al., (1983) and the resulting protein solution concentrated by freeze drying. The purity and nature of the eluted band was analyzed following the teaching of Example 16.

EXAMPLE 19

Analysis of Amino-terminal Sequence of GM-CSF

A sample of GM-CSF, which was purified from a sample of culture supernatant as described in Example 18, was analyzed by the Institut de Recherche en Biotechnologie, Montreal, Canada. Amino-terminal sequencing was performed on an Applied Biosystems Gas Phase Sequenator employing the Edman automated degradation cycling technique (Edman and Begg, 1967). The sequence obtained for the first 9 amino acids of the protein was APARSPSPS which agrees with the expected amino acid sequence.

Although preferred embodiments of the invention have been described in detail, it will be understood by those skilled in the art that variations may be made to the preferred embodiments without departing from either the spirit of the invention or the scope of the appended claims.

LITERATURE CITED

Bibb, M. J., M. J. Bibb, J. M. Ward, and S. N. Cohen. 1985. Nucleotide sequences encoding and promoting expression of three antibiotic resistance genes indigenous to Streptomyces. Mol. Gen. Genet. 199:26–36.

Bibb, M. J., J. L. Schottel, and S. N. Cohen. 1980. A DNA cloning system for interspecies gene transfer in antibiotic-producing Streptomyces. Nature 284:526–531.

Burgess, A. W., C. G. Begley, G. R. Johnson, A. F. Lopez, D. J. Williamson, J. J. Mermod, R. J. Simpson, A. Schmitz, and J. F. Delamarter. 1987. Purification and Properties of Bacterially Synthesized Human Granulocyte-Macrophage Colony Stimulating Factor. Blood 58: 43–51.

Burnette, W. N. 1981. "Western blotting": electrophoretic transfer of proteins from SDS-PAGE to unmidified nitrocellulose and radiographic detection with antibody and radioiodinated protein. Anal. Biochem. 112:195–203.

Carswell, E. A., Old, L. J., Kassel, R. I., Green, S., Fiore, N., and Williamson, B. (1975) Proc. Natl. Acad. Sci. U.S.A. 72, 3666–3670.

Cashman, J. Eaves, A. C. and Eaves, C. J. 1985. Regulated Proliferation of formitive humapoietic proogenitor cells in long-term human marrow cultures. Blood 66: 1002–1005.

Chang, S. 1987. Engineering for protein secretion in gram-positive bacteria. In Methods in Enzymology (eds. Wu. R. and L. Grossman) Academic Press, Inc., New York, N.Y.

Coulombel, L., Eaves, A. C., and Eaves, C. J. 1983. Enzymatic Treatment of long-term human marrow cultures reveals the preferential location of formitive humapoietic proogenitors in the adherent layer. Blood 62: 291–297.

Doggette, P. E., and F. R. Blattner. 1986. Personal access of sequence databases on personal computers. Nucleic Acids Res. 14:611–619.

Edman, P., and Begg, G. 1967. A protein sequenator. Eur. J. Biochem. 1:80–91.

Edwardson, P. A. D., Atkinson, T., Lowe, C. R., and Small, D. A. P. 1986. A new rapid procedure for the preparation of Plasmid DNA. Anal. Biochem. 152:215–220.

Ernst, J. F., J. J. Mermod, J. F. DeLamarter, R. J. Mattaliano, and P. Moonen. 1987. O-Glycosylation and novel processing events during secretion of α-factor/GM-CSF fusions by *Saccharomyces cerevisiae*. Bio/Technol. 5: 831–834.

Gregory, G. J., and Eaves, A. C. 1977. Human marrow cells capable of erythropoietic differentiation in vitro: definition of three erythropoietic colony responses. Blood 49: 855–864.

Hattori, M., Hidaka, S., and Sakaki, Y. 1985. Sequence analysis of a KpnI family member near the 3' end of human B-globin gene. Nucleic Acids Res. 13:7813–7827.

Holmes, D. S. and M. Quigley. 1981. A rapid boiling method for the preparation of bacterial plasmids. Anal. Biochem. 114:193–197.

Hopwood, D. A., M. J. Bibb, K. F. Chater, T. Kieser, C. J. Bruton, H. M. Kieser, D. J. Lydiate, C. P. Smith, J. M. Ward, and H. Schrempf. 1985. Genetic Manipulation of Streptomyces. A Laboratory Manual. The John Innes Foundation, Norwich, UK.

Hunkapiller, M. W., Lujan, E., Ostrander, F., and Hood, L. E. 1983. Isolation of microgram quantities of proteins from polyacrylamide gels for amino acid sequence analysis. In Methods Enzymol. 91:227–236.

Laemmli, U. K. 1980. Cleavage of structural proteins during assembly of the head of bacteriophage T4. Nature 227:680–685.

Lee, F., T. Yokota, T. Otsuka, L. Gemmell, N. Larson, J. Luh, K-I. Arai, and D. Rennick. 1985. Isolation of cDNA for a human granulocyte-macrophage colony-stimulating factor by functional expression in mammalian cells. Proc. Natl. Acad. Sci. USA 82:4360–4364.

Maniatis, T., E. F. Fritsch, and J. Sambrook. 1982. Molecular Cloning. A Laboratory Manual. Cold Spring Harbor Laboratory, Cold Spring Harbor, N.Y.

Miller, J. H. 1972. Experiments in molecular genetics, p. 433. Cold Spring Harbor Laboratory, Cold Spring Harbor, N.Y.

Mizusana, S., S. Nishimura, and F. Seela. 1986. Improvement of the dideoxy chain termination method of DNA sequencing by us of deoxy-7-deazaguanosine triphosphate in place of dGTP. Nucleic Acids Res. 14:1319–1324.

Moonen, P., J. J. Mermod, J. F. Ernst, M. Hirschi, and J. F. DeLamarter. 1987. Increased biological activity of deglycosylated recombinant human granulocyte/-macrophage colony-stimulating factor produced by yeast or animal cells. Proc. Natl. Acad. Sci U.S.A. 84: 4428–4431.

Norrander, J., T. Kempe, and J. Messing. 1983. Construction of improved M13 vectors using oligonucleotide-directed mutagenesis. Gene 26:101–106.

Robbins, P. W., Trimble, R. B., Wirth, D. F., Hering, C., Maley, F., Maley, G. F., Das, R., Gibson, B. W., Royal, N., and Biemann, K. 1984. Primary structure of the Streptomyces enzyme endo-B-N-acetyle-glucosaminidase H. J. Biol. Chem. 259:7577–7583.

Ruff, M. R. and Gifford, G. E. (1981) Infect. Immun. 31, 380–385 and Aggarwal, B. B., Moffat, B., and Harkins, R. N. (1984) J. Biol. Chem. 259, 686–691.

Sanger, F., S. Nicklen, and A. R. Coulson. 1977. DNA sequencing with chain terminating inhibitors. Proc. Natl. Acad. Sci. U.S.A. 74:5463–5467.

Sjostrom, M., Wold, S., Wieslander, A., and Rilfors, L. 1987. Signal peptide amino acid sequences in Escherichia coli contain information related to final protein localization. A multivariate data analysis. EMBO J. 6:823–831.

Thompson, C. J., and G. S. Gray. 1983. Nucleotide sequence of a streptomycete aminoglycoside phosphotransferase gene and its relationship to phosphotransferases encoded by resistance plasmids. Proc. Natl. Acad. Sci. USA 80:5190–5194.

Thompson, C. J., Kieser, T., Ward, J. M., and Hopwood, D. A. 1982. DNA cloning in Streptomyces: resistance genes from antibiotic-producing species. Nature 286:525–527.

Towbin, H., Staehelin, T., and Gordon, J. 1979. Electrophoretic transfer of proteins from polyacrylamide gels to nitrocellulose sheets. Proc. Natl. Acad. Sci. USA 76:4350–4354.

Vieira, J., and J. Messing. 1982. The pUC plasmids, an M13mp7-derived system for insertion mutagenesis and sequencing with synthetic universal primers. Gene 19:259–268.

Wong, G. G., J. S. Witak, P. A. Temple, K. M. Wilkens, A. C. Leary, D. P. Luxemberg, S. S. James, E. L. Brown, R. M. Kay, E. C. Orr, C. Shoemaker, D. W. Golde, R. J. Kaufman, R. M. Hewick, E. A. Wang, and S. C. Clark. 1985. Human GM-CSF: molecular cloning of the complementary DNA and purification of the natural and recombinant proteins. Science 228:810–814.

What is claimed is:

1. A gene expression system comprising a regulatory nucleotide sequence operably linked to a nucleotide sequence encoding a heterologous protein, wherein
    said regulator nucleotide sequence comprises a promoter sequence operably linked to a nucleotide sequence encoding a signal peptide;
    said signal peptide is capable of directing the secretion of said heterologous protein in bioactive form from a host selected from the genus Streptomyces; and
    said signal peptide is a hybrid of signal peptides of the genus Streptomyces.

2. A gene expression system of claim 1 wherein said signal peptide is a hybrid of the signal peptides of *Streptomyces griseus* protease B and *Streptomyces plicatus* endo-B-N-acetylglucosaminidase H.

3. A gene expression system of claim 2 wherein said heterologous protein is granulocyte macrophage colony stimulating factor (GM-CSF).

4. A gene expression system of claim 1 wherein said heterologous protein is granulocyte macrophage colony stimulating factor (GM-CSF).

5. A gene expression system comprising a regulatory nucleotide sequence operably linked to a second nucleotide sequence encoding a heterologous protein, wherein
    said regulatory nucleotide sequence comprises a promoter sequence operably linked to a nucleotide sequence encoding a signal peptide;
    said signal peptide is capable of directing the secretion of said heterologous protein in bioactive form from a host selected from the genus Streptomyces; and
    said signal sequence encodes a hybrid of the signal peptides of *Streptomyces griseus* protease B and *Bacillus subtilis* alkaline protease.

6. A gene expression system of claim 1 or claim 5 wherein
    said promoter sequence permits specific binding of and transcription by a Streptomyces RNA polymerase holoenzyme.

7. A vector capable of transformation and replication in Streptomyces wherein said vector comprises a gene expression system of claim 1 or claim 5.

8. A cell transformed by a recombinant DNA molecule comprising a gene expression system according to claim 1 or claim 5.

9. A gene expression system according to claim 5 wherein said heterologous protein is granulocyte macrophage colony stimulating factor (GM-CSF).

10. A gene expression system according to any of claims 4, 3 or 9, wherein the nucleotide sequence encoding granulocyte macrophage colony stimulating factor (GM-CSF) is the nucleotide sequence in FIG. 1.

11. A vector of claim 7 wherein said vector is pSS2.

12. A process of gene expression comprising a step of transforming a host selected from the genus Streptomyces with a vector according to claim 7.

13. A gene expression system of claim 1, wherein said promoter sequence is from the aminoglycoside phosphotransferase gene of *Streptomyces fradiae*.

14. A process of producing a heterologous protein in a bioactive form that is secreted from a host selected from the genus Streptomyces comprising the steps of:
    (A) transforming a host selected from the genus Streptomyces with a vector according to claim 7;
    (B) growing a culture of the host produced by transformation with said vector under conditions such that said heterologous protein is expressed and secreted in said bioactive form; and
    (C) recovering said heterologous protein from said culture.

15. A process of claim 14 wherein said heterologous protein is granulocyte macrophage colony stimulating factor (GM-CSF).

16. A process according to claim 15, wherein the nucleotide sequence encoding granulocyte macrophage colony stimulating factor (GM-CSF) is the nucleotide sequence in FIG. 1.

17. A process of producing a heterologous protein according to claim 14
    wherein said vector comprises
        a promoter sequence from the aminoglycoside phosphotransferase gene of *Streptomyces fradiae* permitting the specific binding and transcription by a Streptomyces RNA polymerase holoenzyme; and
        a DNA sequence encoding for a signal peptide that is a hybrid of a signal peptide of *Streptomyces griseus* protease B and a signal peptide of *Streptomyces plicatus* endo-B-N-acetylglucosaminidase H.

18. A recombinant DNA molecule encoding a hybrid of the signal peptides of *Streptomyces griseus* protease B and *Streptomyces plicatus* endo-B-N-acetylglucosaminidase H.

19. A recombinant DNA molecule of claim 18 wherein the amino acid sequence of said signal peptide is MRIKRTSNRSNAARRVRTAALALSAAAALVLGSTAASGASA.

20. A recombinant DNA molecule encoding a hybrid of the signal peptides of *Streptomyces griseus* protease B and *Bacillus subtilis* alkaline protease.

21. A recombinant DNA molecule of claim 20 wherein the amino acid sequence of said signal peptide is MRIKRTSNRSNAARRVWISLLFALALIFTMAFGSTSSAQA.

* * * * *

UNITED STATES PATENT AND TRADEMARK OFFICE
CERTIFICATE OF CORRECTION

PATENT NO.    : 5,200,327
DATED         : April 6, 1993
INVENTOR(S)   : Garvin et al.

It is certified that error appears in the above-identified patent and that said Letters Patent is hereby corrected as shown below:

Drawings,
Insert Figure 2 after Figure 1B.

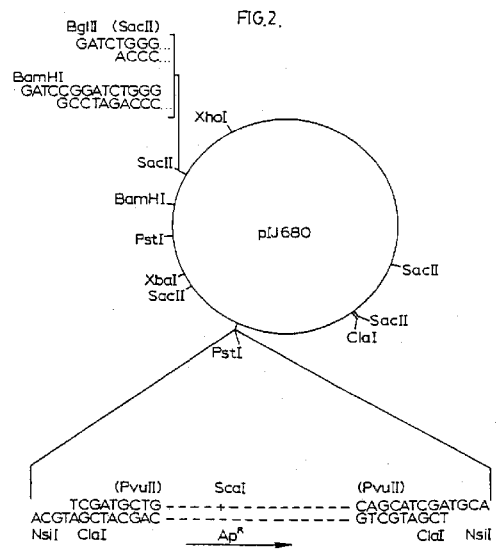

Insert Figures 3A and 4A after Figure 2.

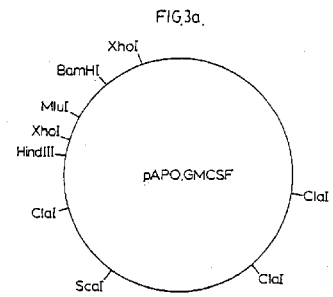

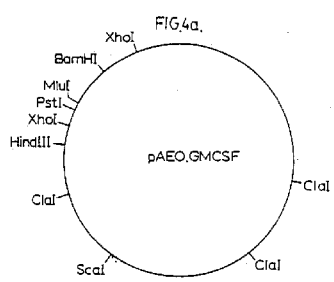

UNITED STATES PATENT AND TRADEMARK OFFICE
CERTIFICATE OF CORRECTION

PATENT NO.     : 5,200,327
DATED          : April 6, 1993
INVENTOR(S)    : Garvin et al.

It is certified that error appears in the above-identified patent and that said Letters Patent is hereby corrected as shown below:

Insert 5A and 6A after Figure 4B (3).

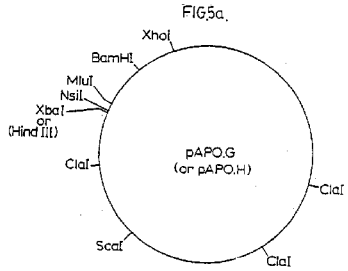

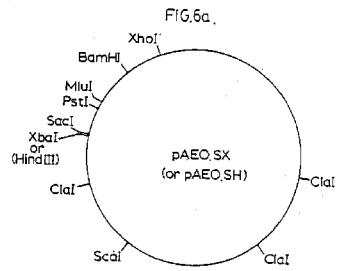

Insert 7a after Figure 6B (3).

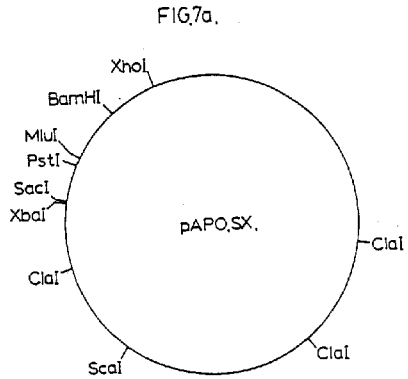

UNITED STATES PATENT AND TRADEMARK OFFICE
CERTIFICATE OF CORRECTION

PATENT NO.    : 5,200,327  
DATED         : April 6, 1993  
INVENTOR(S)   : Garvin et al.

Page 3 of 3

It is certified that error appears in the above-identified patent and that said Letters Patent is hereby corrected as shown below:

Insert Figure 15A after Figure 14.

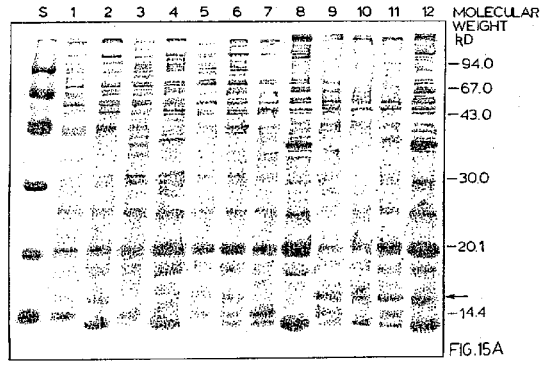

Insert Figure 15B after Figure 15A.

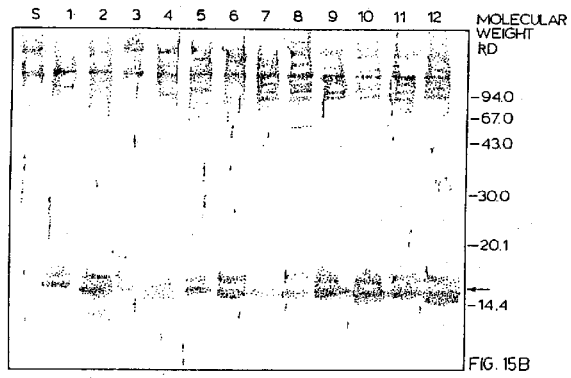

Signed and Sealed this

First Day of April, 2003

JAMES E. ROGAN  
*Director of the United States Patent and Trademark Office*